United States Patent
Cheng

(10) Patent No.: US 7,972,776 B2
(45) Date of Patent: *Jul. 5, 2011

(54) PROTEIN CHIPS FOR HPV DETECTION

(75) Inventor: Shu-Ling Cheng, Fremont, CA (US)

(73) Assignee: OncoHealth Corporation, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/082,740

(22) Filed: Apr. 14, 2008

(65) Prior Publication Data

US 2008/0200344 A1 Aug. 21, 2008

Related U.S. Application Data

(63) Continuation-in-part of application No. 12/009,398, filed on Jan. 19, 2008, now abandoned, and a continuation-in-part of application No. 11/559,366, filed on Nov. 13, 2006, now Pat. No. 7,732,166.

(60) Provisional application No. 60/911,802, filed on Apr. 13, 2007, provisional application No. 60/737,152, filed on Nov. 15, 2005.

(51) Int. Cl.
C12Q 1/70 (2006.01)

(52) U.S. Cl. .......................................................... 435/5

(58) Field of Classification Search ................... None
See application file for complete search history.

(56) References Cited

U.S. PATENT DOCUMENTS

| | | |
|---|---|---|
| 3,633,999 A | 1/1972 | Buckles |
| 4,511,220 A | 4/1985 | Scully |
| 4,619,508 A | 10/1986 | Shibuya et al. |
| 4,744,615 A | 5/1988 | Fan et al. |
| 4,851,978 A | 7/1989 | Ichihara |
| 5,045,447 A | 9/1991 | Minson |
| 5,057,411 A | 10/1991 | Lancaster et al. |
| 5,061,025 A | 10/1991 | Debesis |
| 5,109,465 A | 4/1992 | Klopotek |
| 5,224,200 A | 6/1993 | Rasmussen et al. |
| 5,233,460 A | 8/1993 | Partlo et al. |
| 5,307,207 A | 4/1994 | Ichihara |
| 5,315,427 A | 5/1994 | Rauch et al. |
| 5,328,785 A | 7/1994 | Smith et al. |
| 5,357,365 A | 10/1994 | Ipposhi et al. |
| 5,401,627 A | 3/1995 | Dillner et al. |
| 5,415,995 A | 5/1995 | Schoolnik et al. |
| 5,453,814 A | 9/1995 | Aiyer |
| 5,561,081 A | 10/1996 | Takenouchi et al. |
| 5,591,574 A | 1/1997 | Orth et al. |
| 5,610,733 A | 3/1997 | Feldman et al. |
| 5,621,529 A | 4/1997 | Gordon et al. |
| 5,629,161 A | 5/1997 | Muller et al. |
| 5,662,410 A | 9/1997 | Suganuma |
| 5,665,535 A | 9/1997 | Orth et al. |
| 5,679,509 A | 10/1997 | Wheeler et al. |
| 5,699,191 A | 12/1997 | Fork |
| 5,754,278 A | 5/1998 | Kurtz |
| 5,876,723 A | 3/1999 | Cole et al. |
| 5,888,888 A | 3/1999 | Talwar et al. |
| 5,914,389 A | 6/1999 | Huibregtse et al. |
| 6,013,262 A | 1/2000 | Frazer et al. |
| 6,228,578 B1 | 5/2001 | Impraim et al. |
| 6,355,424 B1 | 3/2002 | Lorinez et al. |
| 6,420,106 B1 | 7/2002 | Gyllensten et al. |
| 6,489,105 B1 | 12/2002 | Matlashewski et al. |
| 6,524,825 B1 | 2/2003 | Mizzen et al. |
| 6,709,832 B1 | 3/2004 | Von Knebel Doeberitz et al. |
| 6,743,593 B2 | 6/2004 | Hu |
| 6,827,933 B2 | 12/2004 | Orth et al. |
| 6,884,786 B1 | 4/2005 | Kieny et al. |
| 6,890,514 B2 | 5/2005 | Mathur et al. |
| 6,900,035 B2 | 5/2005 | Mizzen et al. |
| 6,933,123 B2 | 8/2005 | Hu et al. |
| 7,157,233 B2 | 1/2007 | Fischer et al. |
| 7,361,460 B2 | 4/2008 | Williams et al. |
| 7,399,467 B2 | 7/2008 | Lu et al. |
| 7,455,973 B2 | 11/2008 | Fischer et al. |
| 7,501,261 B2 | 3/2009 | Meijer et al. |
| 7,510,838 B2 | 3/2009 | Fischer et al. |
| 2001/0034021 A1 | 10/2001 | Muller et al. |
| 2004/0170644 A1 | 9/2004 | Mailere et al. |
| 2004/0175695 A1 * | 9/2004 | Debad et al. ........................ 435/5 |
| 2004/0260157 A1 | 12/2004 | Montes et al. |
| 2005/0037017 A1 | 2/2005 | Mizzen et al. |
| 2005/0037342 A1 | 2/2005 | Mathur et al. |
| 2005/0142541 A1 | 6/2005 | Lu et al. |
| 2005/0147621 A1 | 7/2005 | Higgins et al. |
| 2005/0255460 A1 | 11/2005 | Lu et al. |

(Continued)

OTHER PUBLICATIONS

Christensen et al, Virology, 1996, vol. 223, pp. 174-184.*

(Continued)

Primary Examiner — Ali R. Salimi
(74) Attorney, Agent, or Firm — Yi-Shan Yang; Fenwick & West LLP

(57) ABSTRACT

Embodiments of the invention provide methods, assays, and kits for detecting HPV infection, including infection by various HPV genotypes, early and/or late HPV-associated or HPV-specific proteins or antibodies. Detection of HPV DNAs, genomes, and/or oncoproteins by protein chips immunological assays can be used in early clinical screening for HPV infection and general diagnosis for cervical cancer and can be advantageous performed in a multiplexed test. Comparative detection of altered levels of HPV proteins and host proteins can performed in one or more assays. The polypeptides, recombinant proteins, antibodies, nucleic acids, and various detection methods thereof are particularly useful for diagnosing carcinomas of the uterine cervix and those at risk of developing cervical cancer.

7 Claims, 17 Drawing Sheets

U.S. PATENT DOCUMENTS

| | | |
|---|---|---|
| 2005/0255468 A1 | 11/2005 | Ridder et al. |
| 2005/0260566 A1 | 11/2005 | Fischer et al. |
| 2006/0002929 A1 | 1/2006 | Khare et al. |
| 2006/0029943 A1 | 2/2006 | Hermonat et al. |
| 2006/0039919 A1 | 2/2006 | Chang et al. |
| 2006/0121516 A1 | 6/2006 | Norman et al. |
| 2006/0147906 A1 | 7/2006 | Zwerschke et al. |
| 2006/0153864 A1 | 7/2006 | Gissmann et al. |
| 2006/0172285 A1 | 8/2006 | Patterson |
| 2006/0257849 A1 | 11/2006 | Zauderer et al. |
| 2006/0286595 A1 | 12/2006 | Fischer et al. |
| 2007/0048833 A1 | 3/2007 | Sprencher et al. |
| 2007/0059319 A1 | 3/2007 | Carlson et al. |
| 2007/0065810 A1 | 3/2007 | Schlegel et al. |
| 2007/0117167 A1 | 5/2007 | Malinowski et al. |
| 2007/0166699 A1 | 7/2007 | Gissmann et al. |
| 2007/0190062 A1 | 8/2007 | Malinowski et al. |
| 2007/0190529 A1 | 8/2007 | Ridder et al. |
| 2009/0047660 A1 | 2/2009 | Lu et al. |
| 2009/0075377 A1 | 3/2009 | Lu et al. |
| 2009/0148864 A1 | 6/2009 | Fischer et al. |

OTHER PUBLICATIONS

Nomine et al, Protein Engineering, 2001, vol. 14, No. 4, pp. 297-305.*

Bosch F X, Manos M M, Munoz N, et al 1995. Prevalence of human papillomavirus in cervical cancer: a worldwide perspective. J Natl Cancer Inst 87:796-802.

Kiviat N B, and Koutsky L A. 1993. Specific human papillomavirus types as the causal agents of most cervical intraepithelial neoplasia: implications for current views and tr.

Koutsky L A, Holmes K K, Critchlow C W, et al. 1992. A cohort study of the risk of cervical intraepithelial neoplasia grade 2 or 3 in relation to papillomavirus infection.

Kuroda M, Kiyono T, Oikawa K, Yoshida K, Mukai K. 2005. The human papillomavirus E6 and E7 inducible oncogene, hWAPL, exhibits potential as a therapeutic target. Br J Cance.

Lehtinen M, Luukkaala T Wallin K L, et al. 2001. Human papillomavirus infection, risk for subsequent development of cervical neoplasia and associated population attributable.

Li T, Zhao L, Liu Z, Han Y, and Fan D. 2005. Regulation of apoptosis by papillomavirus E6 oncogene. World J Gastroenterol 11:931-37.

Longworth M S, Laimins L A, 2004. Pathogenesis of human papillomavirus in differentiating epithelia. Microbiol Mol Biol Rev 68: 362-72.

Madrigal M, Janicek M F, Sevin B U, et al. 1997. In vitro antigene therapy targeting HPV-16 E6 and E7 in cervical carcinoma. Gynecol Oncol 64: 18-25.

Mougin C, Dalstein V, Pretet J L, et al. 2001. Epidemiology of cervical papillomavirus infections. Recent knowledge. Press Med 30: 1017-23.

Munoz N, Bosch X, Sanjose S, Herrero R, et al. 2003. Epidemiologic classification of human papillomavirus types associated with cervical cancer. N ENGL J MED 348:518-27.

Park T W, fujiwara H, Wright T C. 1995. Molecular biology of cervical cancer and its precursors. Cancer 76: 1902-13.

Wang H L, Lu D W. 2004. Detection of human papillomavirus DNA and expression of p16, Rb, p53 proteins in small cell carcinomas of the uterine cervix. Am J Surg Pathol. 28:.

Walboomers J M, Meichers W J, Manos M M, et al. 1999. Human papilomavirus is a necessary cause of invasive cervical cancer worldwide. J Pathol. 189:12-19.

de Villiers E. M. 1997. Papillomavirus and HPV typing. Clin. Dermatol 15:199-206.

Zur Hausen, H. 2002. Papillomavirus and cancer: from basic studies to clinical application. Nat. rev. Cancer 2: 342-350.

Parkin D M, Pisant P. and ferlay J. 1993. Estimates of the worldwide incidence of eighteen major cancers in 1985. Int J Cancer 54:594-606.

Solomon D, Davey R, Kurman R A, et al. 2002. The 2001 Bethesda Systems. Terminology for reporting results of cervical cytology. JAMA 287:2114-19.

Guimaraes M C, Goncalves M A, Soares C P, et al. 2005. Immunohistochemical expression of p16INK4a and bcl-2 according to HPV type and to the progression of cervical squamous.

Sasagawa T, Rose RC, Azar KK, Sakai A, Inoue M. 2003. Mucosal immunoglobulin-A and -G responses to oncogenic human papilloma virus capsids.Int J Cancer. Apr. 10, 2003;104(3):32.

Fisher, et al. "The Association of Human Papillomavirus Type 16 E6 and E7 Antibodies with stage of Cervical Cancer", Gynecologic Oncology 61, 73-78 (1996) Article No. 0099.

Veress, et al. "Human Papillomavirus DNA and Anti-HPV Secretory IgA Antibodies in Cytologically Normal Cervical Specimens" Journal of Medical Virology 43:201-207 (1994).

Meschede, et al. "Antibodies agains Early Proteins of Human Papillomaviruses as Diagnostic Markers for Invasive Cervical Cancer" Journal of Clinical Microbiology Feb. 1998, pp.

Park, et al. "HPV-16-Related Proteins as the Serolgic Markers in Cervical Neoplasia", Gynecologic Oncology 69, 47-55 (1998).

Viscidi, R. P., S. Yeping, B. Tsuzaki, F. X. Bosch, N. Munoz, and K. Shah. 1993. Serologic response in human papillomavirus-associated invasive cervical cancer. Int. J. Cancer.

Walboomers, et al. "Human Papillomavirus is a Necessary Cause of Invasive Cervical Cancer Worldwide", Jouranl of Pathology 189: 12-19 (1999).

Zumbach, et al "Antibodies Against Oncoproteins E6 and E7 of Human Papillomavirus Types 16 and 18 in Cervical-Carcinoma Patents from Russia", Int. J. Cancer 85, 313-318 (2000).

Sehr, et al. "A generic capture ELISA for recombinant proteins fused to glutathione S-transferase: validation for HPV serology" Journal of Immunological Methods 253 (2001) 153.

Doeberitz, Magnus Von Knebel "New Molecular tools for efficient screening of cervical cancer", Disease Markers 17 (2001) 123-128.

Berumen et al. 2001 Asian-American Variants of Human Papillomavirus 16 and Risk for Cervical Cancer: a Case-Control Study Journal of the National Cancer Institute, vol. 93, No.

Bosch et al. 2002 The causal relation between human papillomavirus and cervical cancer. J. Clin. Pathol.;55;244-265.

Kreimer A R, Clifford G M, Snijders P J, et al. 2005. HPV 16 semiquantitative viral load and serological biomarkers in oral and oropharyngeal squamous cell carcinomas. Int.

Matlashewski G., et al. The expression of human papillomavirus type 18E6 proteins in bacteria and the production of anti-E6 antibodies J Gen Virol (1986) 67: 1909-1916.

Nair, Pillai 2005 Human papillomavirus and disease mechanisms: relevance to oral and cervical cancers Oral Diseases 11,350-359.

Nindl, I., L. Benitez-Bribiesca, J. Berumen, N. Farmanara, S. Fisher, G. Gross, L. Lopez-Carillo, M. Müller, M. Tommasino, A. Vazquez-Curiel, and L. Gissmann 1994. Antibodies.

Snijders et al. 2006 HPV-mediated cervical carcinogenesis: concepts and clinical implications J Pathol 2006; 208: 152-164.

Stoppler, et al. 1996 Natural Variants of the Human Papillomavirus Type 16 E6 Protein Differ in Their Abilities to Alter Keratinocyte Differentiation and to Induce p53 Degra.

Tornesello et al. 2004 Analysis of human papillomavirus type-16 variants in Italian women with cervical intraepithelial neoplasia and cervical cancer. J Med Virol. ;74(1):117-.

Banks et al. 1987 Identification of human papillomavirus type 18 E6 polypeptide in cells derived from human cervical carcinomas J gen Virol (1987) 68:1351-1359.

Oltersdorf et al 1987 Identification of human papillomavirus type 16 E7 protein by monoclonal antibodies J Gen Virol (1987) 68:2933-2938.

Patel et al 1989 Reactivities of polyclonal and monoclonal antibodies raised to the major capsid protein of human papillomavirus type 16 J Gen Vriol 70: 69-77.

Radhakrishna pillai et al 1998 High-risk human papillomavirus infection and E6 protein expression in lesions of the uterine cervix Pathobiology 66(5) 240-246.

Ressler et al 2007 High-risk human popillomavirus E7 oncoprotein detection in cervical squamous cell carcinoma Clin Cancer Res 13(23) 7067-7072.

Seedorf et al 1987 identification of early proteins of the human papillomavirus type 16 (HPV 16) and type (HPV 18) in cervical carcinoma cells EMBO 6(1)139-144.

Fiedler et al 2005 Expression of the high-risk human papillomavirus type 18 and 45 E7 oncoproteins in cervical carcinoma biopsies J Gen Birol 86:3235-3241.

Androphy et al 1987 Identification of the HPV-16 E6 protein from transformed mouse cells and human cervical carcinoma cell lines EMBO 6(4) 989-992.

Andersson et al 2006 Expression of E6/E7 mRNA from high rish human papillomavirus in relation to CIN grade, viral load and p16INK4a Int J oncology 29:70-711.

Keegan et al 2009 Comparison of HPV detection technologies: Hybrid capture 2, preTect HPV proofer and analysis of HPV DNA viral load in HPV 16, HPV 18 and HPV 33 E6/E7 mRNA p.

Inoue et al 1990 A novel monoclonal antibody against squamous cell carcinoma Jpn J Cancer res 81:176-182.

Bjorndal, B. et al., "Expression and Purification of Receptor for Activated C-kinase 1 (RACK1)," Protein Expression & Purification, 2003, vol. 31, pp. 47-55.

Digene Corporation, "hc2 HPV DNA Test," Ref. 5198-1220, 2007, 56 pages.

Mireka, E. et al., "Expression and Purification of His-tagged HPV16E7 Protein Active in pRb Binding," Protein Expression and Purification, 2006, vol. 48, pp. 281-291.

Nomine, Y. et al., "A Strategy for Optimizing the Monodispersity of Fusion Proteins: Application to Purification of Recombinant HPV E6 Oncoprotein," Protein Engineering, 2001, vol. 14, No. 4, pp. 297-305.

PCT International Search Report and Written Opinion, PCT Application No. PCT/US2010/033944, Jul. 2, 2010, 7 pages.

PCT International Search Report, PCT Application No. PCT/US2006/060883, Jul. 18, 2007, 1 page.

Sun, et al., "Comparison of Peptide Enzyme-Linked Immunosorbent Assay and Radioimmunoprecipitation Assay with In Vitro-Translated Proteins for Detection of Serum Antibodies to Human Papillomavirus Type 16 E6 and E7 Proteins" Journal of Clinical Microbiology Sep. 1994 pp. 2216-2220.

Bleul, et al., "Human Papillomavirus Type 18 E6 and E7 Antibodies in Human Sera: Increased Anti-E7 Prevalence in Cervical Cancer Patients" Journal of Clinical Microbiology, Aug. 1991 pp. 1579-1588.

Stacey, et al. "Expression of human papillomavirus type 16 E6 protein by recombinant baculovirus and use for detection of anti-E6 antibodies in human sera", Jouranl of General Virology 1992, vol. 73, pp. 2337-2345.

Studentsov, et al. "Polymer-Based Enzyme-Linked Immunosorbent Assay Using Human Papillomavirus Type 16 (HPV16) Virus-Like Particles Detects HPV16 Clade-Specific Serologic Responses", Journal of Clinical Microbiology Jul. 2003 pp. 2827-2834.

Hagensee, et al. "Detection of Cervical Antibodies to Human Papillomavirus Type 16 (HPV-16) Capsid Antigens in Relation to Detection of HPV-16 DNA and Cervcal Lesions", The Jourrnal of Infectious Diseases 2000; 181: 1234-9.

Wang, et al. "Cervical Mucus Antibodies against Human Papillomavirus Type 16, 18, and 33 Capsids in Relation to Presence of Viral DNA" Journal of Clinical Microbiology Dec. 1996 pp. 3056-3062.

Tjiong, et al. "Antibodies against Human Papillomavirus Type 16 and 18 E6 and E7 Proteins in Cervicovaginal Washings and Serum of Patients with Cervical Neoplasia" Viral Immunology vol. 14, No. 4, 2001 pp. 415-424.

* cited by examiner

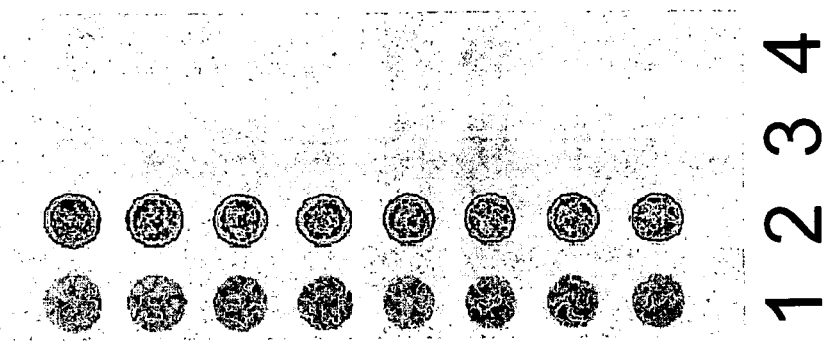
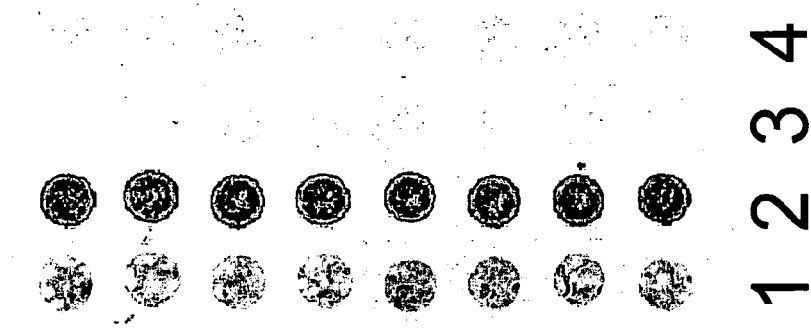
Figure 3

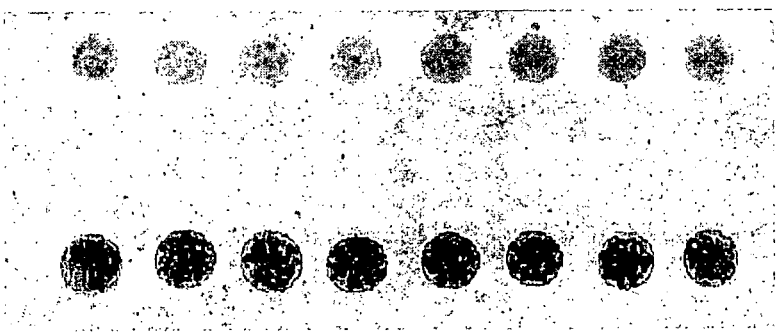
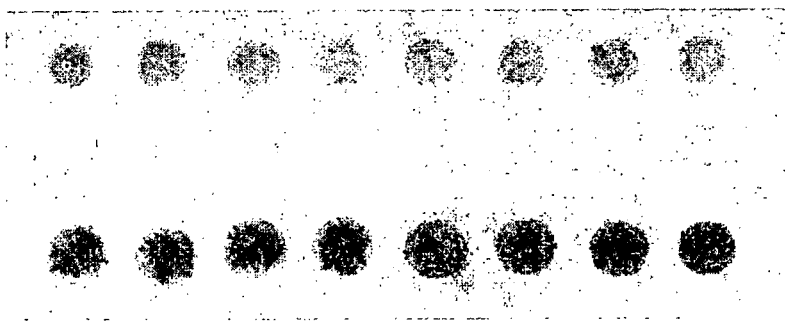
Figure 4

B.
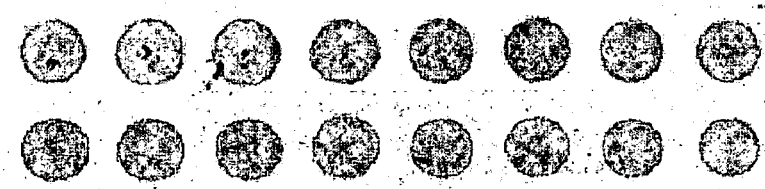
A.
Figure 6

Images of HPV microarray: MAb anti-E6 Detection

Figure 8  *Detect HPV58 and HPV16 E6 protein

Figure 9  *Detect HPV16 E7 protein

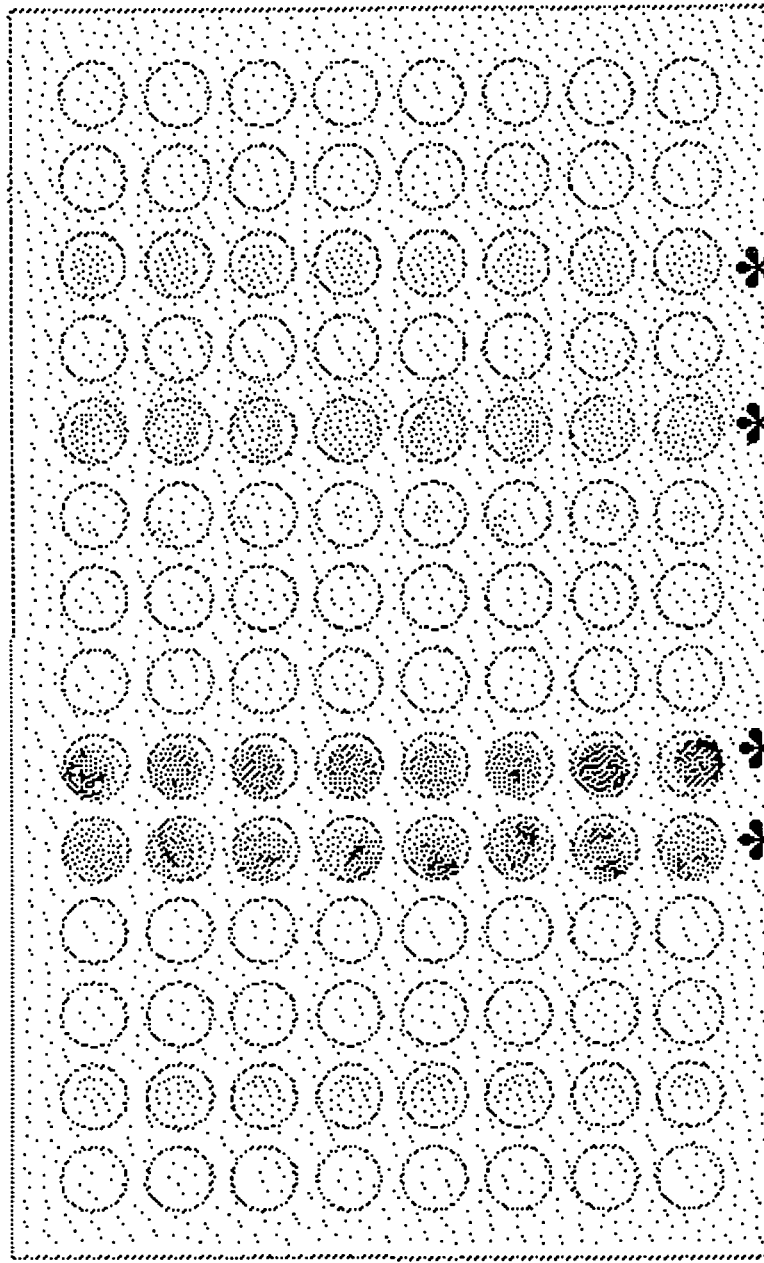
Figure 11 Mab anti-his Detection
*Detect his-tag of HPVE6, E7, and L1 protein Comparison of ELISA assay results and protein chip microarray assay results

| sample # | EIA antibody test | | | | Microarray | | | |
|---|---|---|---|---|---|---|---|---|
| | HPV16 E6-his | HPV 16 E7-his | HPV 16 L1-his | HPV 16 L1 N ter-his | HPV16 E6-his | HPV 16 E7-his | HPV 16 L1-his | HPV 16 L1 N ter-his |
| S1 | | | | | | | | |
| S2 | ++ | ++ | ++ | ++ | | | | |
| S3 | | | | | | + | | |
| S4 | ++ | ++ | ++ | ++ | | ++ | | |
| S5 | ++ | | | | + | + | | |
| S6 | | | | | | + | | |
| S7 | | | | | | | | |
| S8 | | ++ | | | | ++ | | |
| S9 | ++ | ++ | ++ | ++ | ++ | ++ | | |
| S10 | ++ | ++ | ++ | ++ | ++ | ++ | | |
| S11 | ++ | ++ | ++ | ++ | + | + | | |
| S12 | ++ | ++ | ++ | ++ | ++ | | | |
| S13 | ++ | ++ | ++ | ++ | ++ | | ++ | ++ |
| S14 | ++ | ++ | ++ | ++ | ++ | | ++ | ++ |
| S15 | ++ | ++ | ++ | ++ | ++ | | ++ | ++ |
| S16 | ++ | ++ | ++ | ++ | ++ | ++ | + | |
| S17 | ++ | ++ | ++ | | ++ | | + | |
| S18 | ++ | ++ | ++ | | ++ | + | | |
| S19 | ++ | ++ | ++ | | ++ | ++ | ++ | |
| S20 | ++ | ++ | ++ | ++ | ++ | ++ | ++ | ++ |
| S21 | ++ | ++ | ++ | | ++ | ++ | | |
| S22 | ++ | ++ | ++ | | ++ | ++ | ++ | + |

Figure 17

| Pap score 1st and 2nd tests | Cytological Status | Histological or Biopsy follow up analysis | sample from pap test | PCR | HPV16 E6 Ab test | HPV16 E7 Ab test | HPV16 E6 Ag test |
|---|---|---|---|---|---|---|---|
| 4 (1st), 7 (2nd), 17 (3rd) | ASCUS (1st test), LSIL (2nd and 3rd time), possible HPV | Biopsy-HPV w/ atypical change and focal CIN 1 | 1st | Positive | Positive | | Positive |
| 4, 7 | ASCUS (1st), LSIL(2nd) | CIN 1, possible HPV | 2nd | Positive | Positive | | Positive |
| 4, 7 | ASCUS (1st), LSIL(2nd) | CIN 1, possible HPV | 2nd | Negative | Positive | | Negative |
| 4, 7 | ASCUS (1st), LSIL(2nd) | possible HPV infection | 1st | Negative | Positive | | Positive |
| 4 | ASCUS | | 1st | negative | Positive | | negative |
| 4 | ASCUS | | 1st | negative | Positive | Positive | |
| 4 | ASCUS | | 1st | negative | negative | | Positive |
| 4 | ASCUS | | 1st | negative | Positive | | negative |
| 4 | ASCUS | | 1st | negative | negative | | negative |
| 4 | ASCUS | | 1st | negative | negative | | negative |
| 4, 5 | AGUS (1st), LSIL (2nd) | | 2nd | negative | Positive | Positive | negative |
| 5 | AGUS | | 1st | Positive | negative | | negative |
| 7 | LSIL, possible HPV | CIN 1, Biopsy-HPV w/ atypical change | 1st | Negative | Positive | | negative |
| 7, 7 | LSIL, possible HPV | Biopsy-HPV w/ focal CIN 1 | 2nd | Negative | Negative | | Positive |
| 7 | LSIL, possible HPV | CIN 1 | 1st | negative | negative | | negative |
| 14 | Sample with blood | | 1st | negative | Positive | Positive | Positive |
| 14 | Sample with blood | | 1st | negative | negative | Positive | negative |
| 16 | ASCUS, may be HSIL | Biopsy-HPV w/ focal CIN 1 | 1st | Positive | Positive | Positive | |
| 7, 16 | LSIL(1st), ASCUS(2nd HSIL?) | Biopsy-HPV w/ CIN 3 | 2nd | Negative | negative | | negative |
| 17, 10 | LSIL(1st), probably progress into invasive cancer (2nd) | Biopsy w/ CIN 3 | 1st | Negative | Positive | Positive | Negative |

Figure 18

PROTEIN CHIPS FOR HPV DETECTION

CROSS-REFERENCE TO RELATED APPLICATIONS

This application claims benefit of U.S. provisional patent application Ser. No. 60/911,802, filed Apr. 13, 2007. This application is a continuation-in-part of U.S. patent application Ser. No. 12/009,398, filed Jan. 19, 2008 now abandoned and U.S. patent application Ser. No. 11/559,366, filed Nov. 13, 2006, now U.S. Pat. No. 7,732,166 which claims benefit of U.S. provisional patent application Ser. No. 60/737,152, filed Nov. 15, 2005. Each of the aforementioned related patent applications is herein incorporated by reference.

BACKGROUND OF THE INVENTION

Cancer of the uterine cervix or cervical cancer is the second most common cancer in women worldwide. Although screening programs to identify precursor lesions of cervical cancer have contributed to a reduction in mortality and morbidity, 500,000 new cases of invasive cervical cancer are diagnosed worldwide and 230,000 women die of cervical cancer annually. Early detection and diagnosis is critical for survival of cervical cancer.

Infection by human papillomaviruses (HPV) at specific epithelium cells to induce epithelial proliferations plays an important role for cervical carcinogenesis. About 99 percent of confirmed cervical cancer cases are found to be associated with HPV infection with biopsy-confirmed squamous intraepithelial lesions (SIL) or cervical intraepithelial neoplasia (CIN). The incidence of HPV infection, primarily transmitted through sexual contact, is the highest among young women and about 20 millions of sexually active men and women worldwide are currently infected. Approximately 1% of the population has genital warts and 4% of women have cervical precancerous lesions, such as low grade of squamous intraepithelial lesion (LGSIL) or high grade of squamous intraepithelial lesion (HSIL). The presence of these lesions, preferentially observed in women aged 35-40 yrs, is at high risk of progression toward invasive cancer.

There are more than one hundred genetic types of human papillomaviruses identified so far and only a relative few types of HPV, such as HPV-16, -18, -31, -33, -35, -45, -51, -52, -56, and -58, etc., are involved in high risk of progression from HPV infected genital tissue lesions to invasive cervical cancer. Infection with the vast majority of HPV types, such as HPV-6 and -11, etc., are transient with no permanent changes in genital tissues and are at low risk for developing into invasive cervical cancer. However, the development of cervical cancer is a multiple step process that cannot be explained simply by infection with specific types of HPV. Persistent infections with HPVs in high risk group are essential but not exclusively required for the initiation of cervical carcinogenesis. It is found that younger age group women are often infected with HPV; however, clinical information reveals that most latent or asymptomatic infections with high risk HPV types as well as early dysplastic lesions (CIN 1) are usually self-limited and regress spontaneously. There is a high level of correlation between long term persistent infections with only few high-risk HPV types and the induction of advanced CIN 2/CIN 3 lesions and/or the progression to invasive cancer.

One additional event that appears to play a role in tumor progression is the integration of HPV DNA genome into host genome, which frequently disrupts the open reading frame for an early viral gene, E2, resulting in over-expression of two important viral E6 and E7 oncoproteins and transformation of the host cells. Since almost all cervical cancer cases harbor high risk-HPV genomes, screening with HPV infection is important, especially for long term infection with high risk HPV types. Other factors and mutational or secondary genetic events may also be important in the progression and pathogenesis of invasive cervical cancers, including recombination, integration of viral genes to host cell chromosomes, chromosomal rearrangements, loss of constitutional heterozygosity, and proto-oncogene activation.

In the past, screening for cervical cancer was based on conventional cytology by papanicolaou (Pap) smear and suspicious smears were followed up with colposcopy, and/or histological biopsy. The use of cytological screening has led to a remarkable reduction in the mortality of cervical cancer. However, due to subjective test criteria, drawbacks of pap smear tests include difficulty in obtaining samples, poor inter- and intra-observer agreement, a high rate of false negatives (up to 20%) and false positive, the requirements for specialized labs staffed with highly trained personnel, and inability to identify a large proportion of HPV-infected persons. More reproducible assays are needed to improve the current screening method and avoid unnecessary medical intervention and psychological distress for the affected women. Nucleic acid methods, such as "DNA Hybrid Capture", have been developed, but are not ideal primarily due to their high cost, assay operation procedures, and the requirements for facility, equipment, and highly trained personnel. What is needed is a low cost, simple, sensitive and specific assay that can be performed on routine practice of a clinical lab or doctor office.

Attempts to detect the presence of HPV related antibodies in a human subject by ELISA (enzyme linked immunosorbent assays) generally lead to extremely low assay sensitivity and thus can not be developed into a commercially suitable diagnostic test. Most of these ELISA assays target a single viral protein or short peptide fragments, which were not able to interact well or bind strongly and specifically to antibodies from the human subject. The assay specificity and sensitivity are so low such that even using samples from patients confirmed with HPV associated invasive cervical cancer, only 53% of the patient samples were found positive for HPV infection. Thus, there has not been successful ELISA assays available as a diagnostic tool for clinical samples.

Therefore, there is a need to develop methods and assays for the detection of HPV infection.

SUMMARY OF THE INVENTION

Embodiments of the invention generally relate to various methods, detection assays, kits, polypeptides, recombinant proteins, antibodies, and nucleic acids useful for detecting HPV infection, including general HPV infection as well as infection by various HPV genotypes, high risk HPVs and low risk HPVs. In one embodiment, a method of screening a human subject of papillomavirus infection includes obtaining a clinical sample from the human subject, conducting one or more protein chip assays on the clinical sample from the human subject using various HPV recombinant proteins and lab-generated antibodies specific for HPV oncoproteins, and detecting the presence of HPV related oncoproteins and antibodies in the human subject on the surface of one or more protein chips in order to screen for HPV infection.

The format of the protein chips may include various multiplexed microarray formats in a matrix of multiple columns and multiple rows. The various HPV associated recombinant proteins and antibodies may include recombinant proteins and antibodies which show specificity for various HPV genotypes, HPV specific epitopes, HPV proteins encoded by early genes and/or late genes, etc.

The surface of the protein chips for the protein chip assays may be coated with proteins or sandwiched antibodies and can be a surface of a membrane or glass for different visualization and quantification techniques.

In one embodiment, a method of screening a human subject infected with a human papillomavirus includes obtaining one or more clinical samples from the human subject, conducting one or more immunological assays on the clinical sample to detect the presence of an antibody to a papillomavirus viral protein or the presence of the papillomavirus viral protein in the one or more clinical samples, and comparing the results of the one or more immunological assays. The papillomavirus viral protein or antibody may include the early papillomavirus viral protein or antibody, the late papillomavirus viral protein or antibody, and the papillomavirus viral protein or antibody from various HPV genotypes.

The one or more immunological assays may include protein chip assays, EIA assays, among others. The one or more immunological assays may be an antibody test or an antigen test to detect the presence of HPV-specific antibodies or HPV-specific antigens. The results of the protein chip assays and EIA assays can be compared with each other and compared to the results of other clinical assays, pathological assays, cytological assays, nucleic acid hybridization assays, and clinical observations. The one or more immunological assays can be performed independently or concurrently. The one or more immunological assays can be performed on the same or different clinical sample but from the same human subject. Alternatively, the one or more immunological assays can be performed from different human subjects for comparison.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 3A demonstrates the image results of an exemplary immunological protein chip assay for detecting HPV-16 E6 recombinant protein on a protein chip using anti-HPV-16 E6 polyclonal and monoclonal antibodies as spotting antibodies and detecting antibodies and anti-HPV-18 E6 polyclonal antibody as control.

FIG. 3B demonstrates the image results of an exemplary immunological protein chip assay for testing known HPV positive human serum on a protein chip using HPV specific polyclonal and monoclonal antibodies as spotting antibodies and detecting antibodies.

FIG. 4A demonstrates the image results of an exemplary immunological protein chip assay for using a single protein chip coated with a mixture of anti-HPV-16 E6 antibodies and anti-HPV-18 E6 antibodies for detecting HPV-16 E6 recombinant protein.

FIG. 4B demonstrates the image results of an exemplary immunological protein chip assay for using the same protein chip coated with a mixture of anti-HPV-16 E6 antibodies and anti-HPV-18 E6 antibodies as used in FIG. 4A for detecting HPV-18 E6 recombinant protein.

FIG. 4C demonstrates the image results of an exemplary immunological protein chip assay for using the same protein chip coated with a mixture of anti-HPV-16 E6 antibodies and anti-HPV-18 E6 antibodies as used in FIG. 4A for detecting HPV E6 protein from HPV-16 and HPV-18 on known HPV positive human serum.

FIG. 6A demonstrates the image results of an exemplary immunological protein chip assay for using a protein chip coated with anti-HPV-16 E7 polyclonal antiserum as spotting antibodies and anti-HPV-16 E7 monoclonal antibodies for detecting HPV-16 E7 recombinant protein.

FIG. 6B demonstrates the image results of an exemplary immunological protein chip assay for using the same protein chip as used in FIG. 6A which is coated with anti-HPV-16 E7 polyclonal antibodies as spotting antibodies and anti-HPV-16 E7 monoclonal antibodies to show no cross-reactivity with HPV-18 E7 recombinant protein.

FIG. 11 illustrates the image results of an exemplary protein chip microarray for detecting an exemplary anti-his-tagged monoclonal antibody by performing an antibody test using an immunological protein chip assay.

Figure 1:
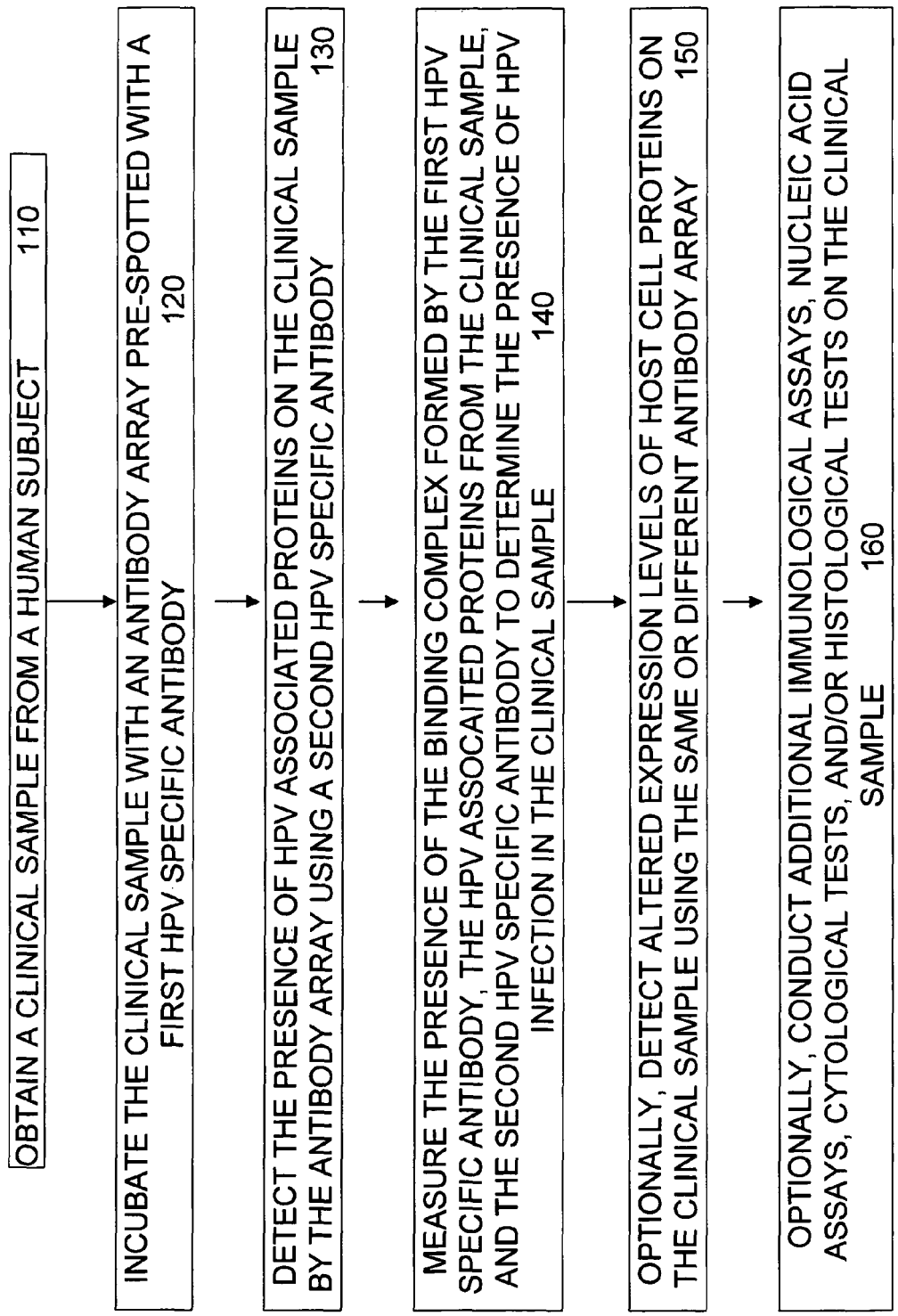
FIG. 1 illustrates an exemplary method according to one or more embodiments.

1:1000) of various exemplary clinical samples (samples #1-#5) according to one embodiment of the invention.

FIG. 17 illustrates an exemplary protein chip microarray for detecting altered expression levels of HPV proteins and host proteins on clinical CIN3 (Cervical Intraepithelial Neoplasia with aggressive form of dysplasia) sample various concentrations (dilution 1:100, 1:500, & 1:1000) of various exemplary clinical samples (samples #1-#5) according to one embodiment of the invention.

FIG. 18 illustrates the results of the antibody tests for E6, the antibody tests for L1, and the PCR test for L1 using cervical samples from 20 human subjects with abnormal Pap smear scores according to one or more embodiments of the invention.

DETAILED DESCRIPTION

Embodiments of the invention provide various methods, detection assays, and kits, polypeptides, recombinant proteins, antibodies, and nucleic acids useful for detecting general HPV infection as well as infection by various HPV genotypes, high risk HPVs and low risk HPVs. One significance is that one single multiplex test can be designed and performed for concurrent screening of HPV infection by various HPV genotypes, high risk HPV groups, low risk HPV groups and/or the detection of the presence of HPV proteins or antibodies related to HPV late genes and early genes. Another application is that the methods and assays described herein can be incorporated into other kits or assays for detecting other bacterial or viral infection, disease diagnosis, or altered expression of host cell proteins.

Detection of HPV DNAs, genomes, early viral proteins, late viral proteins, oncoproteins, and/or capsid proteins from various HPV genotypes can be performed by the method and detection assays as described herein and can be very useful in general clinical screening for HPV infection. Detection of HPV DNAs, genomes, and/or oncoproteins by protein chip immunological assays can be used in early clinical screening for HPV infection and general diagnosis for cervical cancer and can be performed in a single rapid test or in a multiplexed test. Comparative detection of altered levels of HPV proteins and host proteins can be performed in the same or different assays. It can also be used in diagnosing HPV-associated carcinomas of the uterine cervix, as well as those cases associated with epithelial cell abnormalities induced by HPV infection, pre-malignant and malignant HPV-associated epithelial cell lesions, and those at risk of developing HPV-associated cervical carcinoma and adenocarcinoma. The methods as described herein can be used independently or as an adjunct screening tool to conventional cytological papanicolaou smear tests or histological tests and the results thereof can be compared for follow-up patient management.

In one embodiment, a method of screening a human subject of papillomavirus infection includes obtaining a clinical sample from the human subject, and conducting one or more immunological assays on the clinical sample from the human subject using various HPV recombinant proteins and lab-generated antibodies specific for HPV oncoproteins in order to detect and screen for the presence of HPV infection from the presence of HPV proteins and HPV antibodies in the human subject on the surface of one or more protein chips. In another embodiment, the HPV proteins in the human subject are detected using antibodies raised against HPV recombinant proteins, including but not limiting to various polyclonal and monoclonal antibodies against various HPV early and late proteins.

In still another embodiment, the HPV antibodies in the human subject are detected using HPV recombinant proteins. Suitable HPV recombinant proteins are generated using DNA for various early and later HPV genes for various HPV genotypes. For example, a number of HPV recombinant proteins are obtained, including, but not limited to, HPV-16 E6 recombinant protein, HPV-18 E6 recombinant protein, HPV-16 E7 recombinant protein, HPV-18 E7 recombinant protein, HPV-16 L1 recombinant protein, HPV-18 L1 recombinant protein, HPV-16 truncated L1 recombinant protein, HPV-18 truncated L1 recombinant protein, and mixtures and combinations thereof.

The one or more immunological assays as developed herein lend themselves to the high quality and properly purified recombinant proteins encoded by HPV early and late genes, as well as high quality polyclonal and monoclonal antibodies, resulting in immunological assays with very high sensitivity and specificity for screening HPV infection. The one or more immunological assays include, but are not limited to, protein chip assays, antigen assays for papillomavirus proteins, antibody assays for antibodies against papillomavirus proteins, ELISA (enzyme linked immunosorbent assays) assays for papillomavirus immunocomplexes, radioimmunoprecipitation assays, rapid membrane immunochromatographic assays, rapid stick immunochromatographic assays, among others. The one or more immunological assays may be non-invasive with minimal or no additional instrument required. The basic techniques for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals known in the art.

For example, the one or more immunological-based assays may include antibody-based assay having purified papillomavirus proteins coated on a surface, such as the bottom surfaces of a protein chip, a membrane, and/or a microtiter plate. The surfaces that are not coated can be blocked with non-binding proteins. Then, a sample to be tested, such as a sample (samples from human subjects) likely with antibodies against HPV virus or HPV-associated proteins can bind to the surface by binding to the coated purified papillomavirus proteins. The bound antibody-purified papillomavirus protein complex can be detected by a secondary antibody and a number of commercially available detection systems using colormetric, chemiluminescent, or fluorescent substrate. One example of secondary antibody is a horse radish peroxidase-conjugated secondary antibody, such as an antibody against-human immunoglobins (specific for IgG, IgA, etc.). The final results can be read by a microplate reader or visualized by eye if colormetric substrates are used.

As another example, an antigen assay involves coating of a primary antibody, such as a capture antibody or a spotting antibody, having an affinity for binding to an antigen of interest, on a surface, such as bottom surfaces of a protein chip, a membrane and/or a microtiter plate, etc. The antigen of interest may be, for example, a papillomavirus protein, an oncoprotein, a capsid protein, which may be encoded by a HPV viral gene, e.g., an early gene or a late gene, etc. After blocking unbound portions on the surface, the clinical sample to be analyzed can be applied to bind with the capture antibody to form an immunocomplex, which can be detected by another primary antibody or a detection antibody by binding to the antigen of interest. Hence, the two primary antibodies or the pair of the capture antibody and the detection antibody interact with the antigen of interest, much like a sandwich. The capture or spotting antibody can be the same or different antibody as the detection antibody as long as the two antibodies can specifically bind to the antigen of interest, e.g., a HPV viral protein, a HPV oncoprotein, a capsid protein, among others.

Next, the sandwiched bound antibody-antigen complex can be detected by a secondary antibody, which have an affinity for the detection antibody and facilitate measurement by a standard immunological complex detection system using colorimetric, chemiluminescent, fluorescent and many different kinds of substrates. The final readouts or visualizations can be performed by an instrument with appropriate light absorbance readers or directly visualized by eye and compared to the results to a control sample. Positive results indicate binding of the antigen of the interest to the primary antibodies, the capture antibody, and the detection antibody, and thus the presence of the antigen of interest in the clinical sample. In the contrary, negative results indicate no binding of the antigen of the interest to the primary antibodies and thus the absence of the antigen of interest in the clinical sample.

The one or more immunological assays can be used to detect at least three kinds of target proteins of interest, including, but not limited to, antigen, antibody, and antigen/antibody immunocomplex (also referred hereafter as antigen tests, antibody tests, and antigen/antibody immunocomplex tests, respectively), among others. The formats of the one or more immunological assays may be a microplate format (e.g., 32 wells, 48 wells or 96 wells), a vertical or lateral membrane-based rapid test, and a protein chip with multiple spots or multiplexed. The principles of the assays are the same as described above except detection systems vary depending on the substrate chosen for analyzing the results in different readouts or forms by an instrument specifically designed for the assays. In addition, the procedures, conditions, and binding specificity developed in one type of immunological assay in one format can be adapted into a different format of the same or a different immunological assay, and/or a different immunological assay in the same or a different format.

For example, in a protein chip assay, the surface for proteins to be coated/bound to may be, for example, a surface-chemistry treated glass or membrane, which can be covalently or non-covalently bind or coat with capture agents or proteins thereto. A spotting machine with fine pins dipped with capture agents, such as the recombinant proteins, antigens, antibodies, or other proteins, in suitable buffers is generally used to facilitate binding of such proteins or antibodies to the treated surface. Like other surfaces described in the microtiter plate format, the spotted and thus captured proteins or antibodies bind strongly to the surface-chemistry treated surface of a protein chip and remain on the treated surface to allow the interaction and specific binding of the captures proteins with target proteins, antibodies, or antigens, even after several washings of removing non-specific binding, to be detected with a detection system having a secondary antibody conjugated with Cy3 or Cy5. The detection of specific interaction is obtained and measured by the intensities of the spotted/dipped images via a microarray scanner.

More than one proteins can be initially spotted and thus bound on the treated surface to specifically capture target proteins, antibodies, or antigens, and thus, it is possible to interact with and bind to multiple proteins or targets (multiplexed) in a single sample and binding of at least one of the multiple proteins or targets on the surface of the protein chip can be detected, performing one assay which is essentially many assays combined together. Thus, the protein chip assays, as compared to other assay formats, advantageously provides higher sensitivity and a multiplex format with only very minimal amount of samples required, such as less than 50 μl or less than 10 μl. Such feature of being able to detect multiple binding activities with minimal sample requirement makes it feasible to conduct many assays in one for certain disease tissues where the amount of accessible samples is very limited.

The one or more immunological assays using antibodies and purified recombinant proteins derived from HPV early and/or late genes as obtained herein serve as reliable indicators whether HPV infection has occurred. In addition, HPV associated malignancy or pre-malignant cell transformation can be assayed. One of the most useful aspects of the invention is in diagnosing cervical carcinoma, squamous cell carcinoma and adenocarcinoma as well as any epithelial cell abnormality associated with oncogenic HPV infection including koilocytosis, hyperkeratosis, precancerous conditions encompassing intraepithelial neoplasias or intraepithelial lesion, high-grade dysplasias, and invasive or malignant cancers.

FIG. 1 illustrates a method 100 of screening a human subject for papillomavirus infection. At step 110, a clinical sample from a human subject is obtained. The clinical sample may include, but are not limited to, genital swabs, general fluid, cervical cells, cervical tissues, cervical swabs, body fluids, serum, blood, urine, lesion sites, and tumors, among others. The clinical sample may be obtained by various methods known in the art. For example, genital swabs from clinical hospitals can be provided, together with Pap smear scores, cytological results, and demographic history of the clinical samples from human subjects, either normal subjects or patients.

As an example, protein chip arrays can be performed as an antibody array, pre-spotted with antibodies for binding to a target protein; or alternatively, an antigen array, pre-spotted with proteins or antigens for pulling down antibody from a sample. The protein chip array can be arranged in a spotting format for detecting various HPV genotypes or in a combinatorial detection format for diagnosis of HPV infection and other diseases at the same time.

At step 120, the clinical sample is incubated with a protein chip array pre-spotted with a first HPV specific antibody. For example, the first HPV specific antibody may be a mixture containing one or more antibodies, including, but not limited to, polyclonal antibody against HPV-16 E6 recombinant protein, polyclonal antibody against HPV-18 E6 recombinant protein, polyclonal antibody against HPV-16 E7 recombinant protein, polyclonal antibody against HPV-18 E7 recombinant protein, polyclonal antibody against HPV-16 L1 recombinant protein, polyclonal antibody against HPV-18 L1 recombinant protein, polyclonal antibody against HPV-16 truncated L1 recombinant protein, polyclonal antibody against HPV-18 truncated L1 recombinant protein, monoclonal antibody against HPV-16 E6 recombinant protein, monoclonal antibody against HPV-18 E6 recombinant protein, monoclonal antibody against HPV-18 E7 recombinant protein, monoclonal antibody against HPV-18 E7 recombinant protein, monoclonal antibody against HPV-16 L1 recombinant protein, monoclonal antibody against HPV-18 L1 recombinant protein, monoclonal antibody against HPV-16 truncated L1 recombinant protein, monoclonal antibody against HPV-18 truncated L1 recombinant protein, and mixtures and combinations thereof. The first HPV specific antibody is used to bind target HPV proteins, such as various HPV early and late proteins present in the clinical sample. For example, HPV-16 E6 protein, HPV-18 E6 protein, HPV-16 E7 protein, HPV-18 E7 protein, HPV-16 L1 protein, HPV-18 L1 protein, and mixtures and combinations thereof, from a sample can be detected by various HPV specific antibodies as used herein.

In one embodiment, each spot on the antibody array is pre-spotted with a first HPV specific antibody which is a mixture of two or more HPV antibodies specific for different recombinant HPV proteins from the same HPV genotypes. For example, the first HPV specific antibody can include a mixture of one or more antibodies specific for HPV-16 E6 protein, HPV-16 E7 protein, and/or HPV-16 L1 protein in order to detect HPV-16 infection. As another example, the first HPV specific antibody can include one or more antibodies specific for HPV-18 E6 protein, HPV-18 E7 protein, and/or HPV-18 L1 protein in order to detect HPV-18 infection In another embodiment, each spot on the antibody array is pre-spotted with a first HPV specific antibody which is a mixture of two or more HPV antibodies specific for the same HPV proteins from different HPV genotypes. For example, the first HPV specific antibody can include a mixture of one or more antibodies specific for HPV-16 E6 protein and HPV-18 E6 protein in order to detect infection by high risk HPV. As another example, the first HPV specific antibody can include a mixture of one or more antibodies specific for HPV-6 E6 and HPV-11 E6 protein in order to detect infection by low risk HPV.

In another example, the first HPV specific antibody can include a mixture of one or more antibodies specific for HPV-16 E6 protein, HPV-18 E6 protein, HPV-6 E6, and/or HPV-11 E6 protein in order to detect the presence of high risk and low risk HPV infection. As another example, the first HPV specific antibody can include a mixture of one or more antibodies specific for HPV-16 L1 protein, HPV-18 L1 protein, HPV-6 L1, and/or HPV-11 L1 protein in order to detect the presence of general HPV infection regardless of high risk and low risk HPV types.

At step 130, the presence of HPV proteins on the clinical sample is detected by the antibody array using a second HPV specific antibody. The first and the second HPV specific antibodies can be the same or different antibody clones. In one embodiment, the first and the second HPV specific antibodies are different.

At step 140, the presence of the binding complex formed by the first HPV specific antibody, the HPV proteins from the clinical sample, and the second HPV specific antibody is detected to an increased level as compared to a normal background level in order to determine the presence of HPV infection in the clinical sample. Binding of any HPV-associated proteins/antigens in a biological sample to antibodies obtained herein using the one or more recombinant proteins, and/or binding of any immunocomplexes of HPV-associated proteins in the sample to the one or more antibodies as obtained herein, indicates the presence of HPV infection protein in the sample.

In one embodiment, the human papillomavirus may be, for example, high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, etc. High risk human papillomaviruses include, but not limited to, HPV-16, HPV-18, HPV-31, HPV-33, HPV-35, HPV-39, HPV-45, HPV-51, HPV-52, HPV-58, HPV-59, and HPV-68, among others. Low risk human papillomaviruses include, but not limited to, HPV-6, HPV-11, HPV-42, HPV-43, HPV-44, HPV-53, HPV-54, and HPV-55, among others.

Papillomaviruses are DNA viruses with a DNA genome, a non-enveloped virion, and an icosahedra capsid. The double-stranded, circular HPV DNA genome contains one coding region for late genes, one coding region for early genes, and a non-coding upstream regulatory region with binding sites for the various transcription factors controlling expression of early and late genes. Two separate open reading frames in the late gene coding region encode viral capsid proteins L1 and L2. Capsid protein L1 is the major capsid protein that is highly conserved among different HPV types. Eight open reading frames in the early gene coding region encode eight early viral proteins, designated E1, E2, E3, E4, E5, E6, E7, and E8. Early proteins E6 and E7 are oncoproteins critical for host cell immortalization and transformation as well as for long term viral replication and survival.

Infection by high risk HPVs requires two early viral proteins, E6 and E7, which are oncoproteins because they transform cells in vitro and their presence is needed to maintain malignancy. Inhibition of E6 and E7 expression in precancerous or cancer cervical tissue blocks invasive cancer progression. Inside the host tissues, E6 and E7 oncoproteins work by negatively blocking the activities of endogenous host cellular regulatory proteins, p53 and retinoblastoma (Rb) tumor suppression proteins, respectively, to cause inhibition of apoptosis and deregulation of cell cycle, leading to development of cervical cancers. E6 oncoprotein binds to p53, a cellular factor that protects cells against DNA damage and regulates apoptosis, to induce degradation of p53. By reducing the levels of p53 protein, E6 oncoprotein prevents tumor cell death. E7 oncoprotein binds to Rb to induce degradation of Rb, disrupt normal cell cycle, and cause cellular proliferation. The E7 oncoprotein further destabilizes cell control through its interaction with the cyclin-dependent kinase inhibitor protein, p21. HPV E6 and E7 oncoproteins are found to be continuously produced in transformed genital tissues. These interactions set the stage for controlling host cell proliferation and differentiation (i.e., transformation), the first step in the conversion of normal cells to pre-neoplastic cells and ultimately to the full expression of cancer malignancy.

One additional event that appears to play a role in tumor progression is the integration of HPV DNA into the host genome, which frequently disrupts the open reading frame for E2, resulting in over-expression of the E6 and E7 oncoproteins and possibly causing instability of host genome. Additional cofactors and mutational events may be important in the pathogenesis of invasive cervical cancers and may include chromosomal rearrangements, loss of constitutional heterozygosity, and proto-oncogene activation.

Both HPV-16 and HPV-18 are shown to immortalize human keratinocytes in culture and are by far the most common high risk HPV types that induce invasive cervical cancer. Infection by HPV-16 type alone is associated with over 50% of cervical cancer cases, mostly resulting in squamous cell carcinoma. HPV-18 infection is more likely to induce adenocarcinomas. Some studies have indicated that adenocarcinomas in cervical tissues produce more aggressive forms of cancer with a less favorable outcome than cancers resulting from squamous cell carcinomas. This suggests that individuals with HPV-18 infection may have a much poorer prognosis than those with any other form of HPV infection.

To test the hypothesis that E6 and E7 play an active role in the maintenance of the malignant phenotype and may be ideal targets for anti-gene therapy, studies showed antiproliferative effects of phosphorothioate oligodeoxynucleotides (oligos) targeting HPV-16 E6 and E7 in cervical cancer cell lines and primary tumor explants. These specific antiproliferative effects suggest that HPV-16 E6 and E7 sequences play an active role in the malignant growth properties of cervical cancer cells and may be ideal targets for anti-gene therapy. Expression of two viral oncogenes, E6 and E7, in epithelial stem cells is required to initiate and maintain cervical carcinogenesis and results in significant over-expression of the cellular p16INK4a protein.

Variants of HPV-16 have also been found to produce differences in the aggressiveness of the forms of cervical cancer they induce. For example, Asian-American HPV-16 variants are more oncogenic than European HPV-16 variants. It has also been shown that Asian-American and African HPV-16 variants are more likely to produce invasive cervical cancer than European HPV-16 variants. The more aggressive nature of some of these variants may be related to variations in the amino acid sequences of the oncoproteins produced by the viruses. E6 protein from Asian-American HPV-16 variants is shown to be stronger in transforming keratinocytes and in suppressing p53 expression than E6 protein from European HPV-16 variants while these E6 proteins differ only in several amino acids in their sequences. Thus, in diagnosing high risk patients for invasive cervical cancer progression, it is important to identify not only the specific HPV type infecting the patient, but also the variant type of the infecting HPV.

In one embodiment, the early gene that can be used herein may include papillomavirus E6 genes, papillomavirus E7 genes, among others. In another embodiment, the late gene that can be used herein may include papillomavirus L1 genes, papillomavirus L2 genes, among others.

One aspect of the invention provides recombinant proteins, such as a recombinant hybrid protein containing a full length sequence of HPV oncogenic proteins, e.g., full-length E6, E7, and/or L1 polypeptide sequence, which have been found very difficult to obtain and purify due to undesirable aggregation during protein purification, protein instability, low levels of expression, low immunogenic responses of purified proteins. For example, many early E6 oncoproteins contain many cysteine amino acids and thus the correct topography of the E6 oncoproteins requires formation of many disulfide bonds properly. In addition, it was known that certain immunological assays using small peptides of early E6 and E7 proteins results in extremely low assay specificity and sensitivity and thus unsuitable as commercialized diagnostic tools.

At step 150, optionally, altered expression levels of host cell proteins from the clinical sample are compared to the levels of the host cell proteins from normal clinical sample by conducting the same or different antibody array. Accordingly, the expression levels of host cell proteins, which are affected by HPV infection, can be detected.

HPV proteins are found to interact with a variety of host cell proteins and comparison of altered expression levels of these HPV interacting host cell proteins helps confirm HPV infection and its progression into various stages of dysplastic lesions and cervical cancer. For example, HPV E6 and E7 proteins are important factors in cellular transformation induced by high risk HPV. The expression of E6 and E7 in replication competent basal cells seems to be tightly suppressed by certain cellular factors that have not been identified yet.

In high grade CIN lesions, E6 and E7 are strongly expressed in host basal epithelial cells and interfere substantially with cell cycle control of these replication competent host cells. Expression of HPV oncoproteins interferes with G1-S-Phase regulation in host cells. The HPV E6 and E7 proteins target a plethora of cellular interactions, such as the inactivation of pRB by E7 and the degradation of p53 by E6. High level of HPV E7 proteins inactivates pRB and leads to disruption of E2F-Rb binding. Usually, binding of pRB to E2F blocks E2F driven cell cycle activation. In replicating cells, E2F is regulated by phosphorylation of RB. RB phosphorylation is normally mediated by cyclin dependent kinases (CDK4, CDK6) that are controlled by several kinase inhibitors (INKs).

As a result of the loss of RB/E2F repression and the strong activation by free E2F, the expression of a host cell protein, p16INK4a, is strongly overexpressed. In addition, S-phase genes are continuously activated since the p16INK4a mediated repression of Cdk4/6 has no downstream effect on pRB host cell protein. Since the release of E7-dependent E2F is not mediated by phosphorylation of pRB, the counter-regulatory p16INK4a expression has no effect on the activated cell cycle. Under physiological conditions p16INK4a is expressed when cells undergo a genomic stress situation such as substantial shortening of telomeres in ageing tissues. Also, apoptosis is abrogated by HPV E6 mediated degradation of p53. The overexpression of the cyclin dependent kinase (CDK) inhibitor, p16INK4a, is a direct consequence of deregulated HPV oncogene expression.

In addition, host cell proteins important for proliferation and host cell genome replication may be overexpressed as a result of HPV infection. These host cell proteins include, ki67 (MIB-1), MYC cellular oncogene, Cyclin proteins (e.g., cyclin A, B, E, etc.), CDKN2A/p16INK4a, telomerase (e.g., TERC), replication complex proteins (e.g., MCM5, CDC6, topoisomerase II alpha (TOP2A), MCM2, mini-chromosome maintenance proteins 2, 4, and 5, etc.).

Other host cell proteins affected by HPV infection may include host cellular stress and invasion proteins, such as heat shock protein (e.g., $HSP_{40}$, $HSP_{60}$, $HSP_{70}$), carbonic anhydrase (e.g., CA9/MN antigen). Also, host cell proteins that enhance viral oncogene activity can be affected by HPV infection and these proteins include TSLC1, DAPK1, RARB, TWIST1, brn-3s transcription factor, among others. In addition, survivin protein which is involved in cell cycle and apoptosis regulation can be affected by HPV infection. The expression of VEGF can be upregulated by HPV E6 protein, which is independent from E6 mediated p53 degradation.

Accordingly, examples of host cell proteins whose expression levels may be altered by HPV infection include, but are not limited to, p16INK4a, cyclin dependent kinase inhibitors, pRB, p53, E2F, E2F activated cell cycle proteins, cyclin dependent kinases, CDK4, CDK6, S-phase genes, Ki-67 (MIB-1), MYC protein, cyclin-A, cyclin-B, cyclin-E, telomerase-TERC, MCM2 protein, TOP2A protein, heat shock protein 40 ($HSP_{40}$), heat shock protein 60 ($HSP_{60}$), heat shock protein 70 ($HSP_{70}$), CA9/MN protein, laminin 5, laminin proteins, brn-3a, CDK N2 protein, topoisomerase 2A, mini-chromosome maintenance proteins-2, mini-chromosome maintenance proteins-4, mini-chromosome maintenance proteins-5, survivin protein, VEGF protein, p27 (kip1) protein, p21 (waf) protein, and combinations thereof.

Changes in the expression levels among these proteins affected by HPV infection (e.g., E6, E7, p53, Rb, p16INK4a, among others) serve as a signature for high risk of contracting cervical cancer. Elevated levels of HPV-associated viral proteins, viral antigens, and host cells proteins (e.g., E6 proteins, E7 proteins, p16INK4a, E2F, Ki-67 (MIB-1), MYC protein, CDK4, cyclin-A, cyclin-B, cyclin-E, telomerase-TERC, MCM2 protein, TOP2A protein, heat shock protein 40 ($HSP_{40}$), heat shock protein 60 ($HSP_{60}$), heat shock protein 70 ($HSP_{70}$), CA9/MN protein, laminin 5, laminin proteins, brn-3a, CDK N2 protein, topoisomerase 2A, mini-chromosome maintenance proteins-2, mini-chromosome maintenance proteins-4, mini-chromosome maintenance proteins-5, survivin protein, VEGF protein), and reduced levels of host cell proteins (e.g., p53, RB, p27 (kip1), and p21 (waf), etc.) confirm the human subjects of not just HPV infection but also at high risk of contracting cervical cancer. On the contrary, unchanged levels of p53 and RB in the human subjects but elevated levels of HPV-associated viral proteins or antigens may indicate a general HPV infection and cervical cancer is not yet progressed.

At step 160, one or more additional immunological assays, nucleic acid assays, cytological tests and/or histological tests are conducted on the clinical sample. The nucleic acid hybridization assay conducted on the clinical sample to detect the presence of a papillomavirus genome in the clinical sample from the human subject may include, but are not limited to, polymerase chain reactions (PCR), nucleic acid hybridization assays, DNA chip assays, radioactive nucleic acid hybridization and detection assays, and non-radioactive nucleic acid hybridization and detection assays.

The method as described herein may also include performing a cytological papanicolaou smear assay on the clinical sample and comparing the results of the cytological papanicolaou smear assay with the results of the one or more immunological assays. Since HPV can't be cultured efficiently, and the clinical performance of serological assays is poor, diagnosis of HPV infection is almost entirely based on molecular tools. Nucleic acid amplification techniques such as PCR, nucleic acid-sequence based amplification, and advances in nucleic acid-based techniques, including hybrid capture technology (one example is a commercially available Digene hybrid capture II test from Digene Corporation, Gaithersburg, Md.), can be used in addition to the one or more immunological assays as described herein as a molecular screening tool for HPV infection.

As an example, the immunological assays for detection of HPV proteins, such as E6, E7, L1, etc., or immune response thereof due to HPV infection can be performed in high throughput ELISA screening assays, one step rapid immunological screening assays, and additional multiplexed protein chip assays, etc., and combinations thereof. Embodiments of the invention provides one or more assays, including antibody, antigen, or immunocomplex assays developed to detect HPV viral proteins encoded by early genes (e.g., E6 and E7) and late genes (e.g., L1). In addition, the developed antibody, antigen, or immunocomplex assays for E6, E7, L1, protein or their antibodies thereof in one format, for example, a microplate format, can be adapted into a one-step immunochromatographic assay for the direct measurement of E6, E7, L1 proteins or antibodies induced by HPV infection.

The one-step immunochromatographic assay is a simple, fast, and easy to operate assay, which can be conveniently developed for point-of-care use. In general, there is simply mixing of a sample to be tested with a detection antibody as developed herein, the mixture can be applied onto or is already fixed on a surface (e.g., a membrane or a glass) for a pre-determined reaction time (e.g., in minutes, etc.) at optimized incubation temperature, such as at room temperature. The reaction can be optimized to be short for convenience depending on the quality of the detection antibody used and the assay reaction conditions. Thus, a rapid immunological test with short waiting time period can be performed and the assay results is generally designed to be visually scored without the need of any detection instruments.

As another example, for a rapid immunological test, the surface for an antibody or a protein to be coated thereon can be membrane-based, and the binding capacity of the rapid immunological test differs, depending on the types of target proteins, antibodies, or antigens and background non-specific protein contained in the samples with the target protein, antibodies, or antigens. At least two formats of the rapid immunological test can be used, a vertical rapid immunological test and a lateral rapid immunological test.

The vertical rapid immunological test is conducted in a device having a membrane as a capturing/binding surface for coating or spotting a capture agent thereon. The device further contains a pad underneath the membrane to allow the samples and assay reagent to flow through the membrane. Any target proteins, antibodies, or antigens that are contained in the samples and specifically interact and bind to the capture agent will not flow through and will be captured and retain on the surface of the membrane, even after several washings to remove non-specific binding. A secondary antibody conjugate with HRP or others can be applied on the surface for detecting any protein-antibody complexes retained on the surface and being visualized by colormetric substrates.

The lateral rapid immunological test is a one-step test using a membrane strip with the capture proteins or antibodies already applied/coated to designated positions on the surface thereof. The only step the test requires is to combine obtained samples having the target proteins or antibodies with a detecting antibody conjugated with collateral gold particles and directly apply the combined mixtures to the membrane strip for the sample fluid to laterally flow through the membrane strip until the designated positions of the surface of the membrane strip. The capture-target-detecting protein-antibody immuno-complexes can be formed and retained on the designated positions where the capture proteins or antibodies are coated. Positive results can be visualized at these designated positions and no washing or separation is required, thus called one-step. The whole procedure for the test takes only minutes, for example, less than 15 minutes, and thus the test is also referred to as a one-step rapid test.

Figure 2:
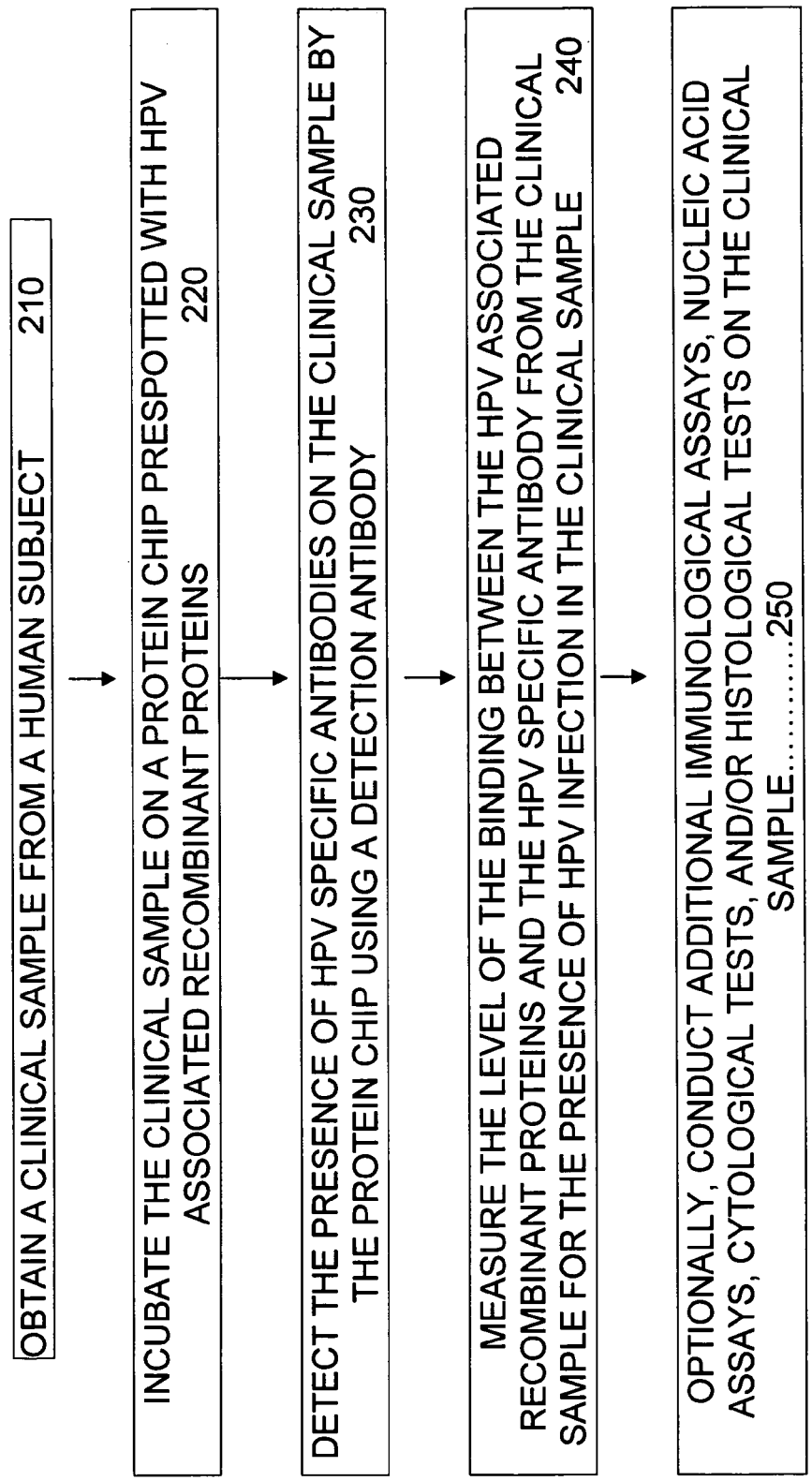
FIG. 2 illustrates another exemplary method according to one or more embodiments.

FIG. 2 illustrates a method 200 of screening a human subject for papillomavirus infection. At step 210, a clinical sample from a human subject is obtained. At step 220, the clinical sample is incubated with an antigen array pre-spotted with a mixture of one or more HPV recombinant proteins. One or more recombinant proteins encoded by an early gene and/or a late gene of a papillomavirus are obtained.

The one or more HPV recombinant proteins can be, for example, HPV-16 E6 recombinant protein, HPV-18 E6 recombinant protein, HPV-16 E7 recombinant protein, HPV-18 E7 recombinant protein, HPV-16 L1 recombinant protein, HPV-18 L1 recombinant protein, HPV-16 truncated L1 recombinant protein, HPV-18 truncated L1 recombinant protein, and mixtures and combinations thereof, in order to detect the presence of the HPV specific antibodies from the clinical sample. HPV specific antibodies present in the clinical sample may include, but are not limited to anti-HPV-16 E6 antibody, anti-HPV-18 E6 antibody, anti-HPV-16 E7 antibody, anti-HPV-18 E7 antibody, anti-HPV-16 L1 antibody, anti-HPV-18 L1 antibody, and mixtures and combinations thereof.

In one embodiment, each spot on the antigen array is pre-spotted with a mixture of two or more HPV recombinant proteins from the same HPV genotypes. For example, each spot can be spotted with a mixture of HPV-16 E6 recombinant protein, HPV-16 E7 recombinant protein, HPV-16 L1 recombinant protein, and/or HPV-16 truncated L1 recombinant protein for detecting HPV-16 infection. As another example, each spot can be spotted with a mixture of HPV-18 E6 recombinant protein, HPV-18 E7 recombinant protein, HPV-18 L1 recombinant protein, and/or HPV-18 truncated L1 recombinant protein for detecting HPV-18 infection.

In another embodiment, each spot on the antigen array is pre-spotted with a mixture of two or more HPV early oncoproteins from different HPV genotypes. In still another embodiment, each spot on the antigen array is pre-spotted with a mixture of two or more HPV late oncoproteins from different HPV genotypes. For example, each spot can be spotted with a mixture of HPV-16 E6 recombinant protein, HPV-18 E6 recombinant protein, HPV-16 E7 recombinant protein, HPV-18 E7 recombinant protein, HPV-6 E6 recombinant protein, HPV-11 E6 recombinant protein, HPV-6 E7 recombinant protein, and/or HPV-11 E7 recombinant protein, for detecting early stage HPV infection. For example, each spot can be spotted with a mixture of HPV-16 L1 recombinant protein, HPV-18 L1 recombinant protein, HPV-16 truncated L1 recombinant protein, and/or HPV-18 truncated L1 recombinant protein for detecting late stage HPV infection.

As another example, each spot can be spotted with a mixture of HPV-16 E6 recombinant protein, HPV-18 E6 recombinant protein, HPV-16 E7 recombinant protein, HPV-18 E7 recombinant protein, HPV-16 L1 recombinant protein, HPV-18 L1 recombinant protein, HPV-16 truncated L1 recombinant protein, and/or HPV-18 truncated L1 recombinant protein for detecting high risk HPV infection. As another example, each spot can be spotted with a mixture of HPV-6 E6 recombinant protein, HPV-11 E6 recombinant protein, HPV-6 E7 recombinant protein, HPV-11 E7 recombinant protein, HPV-6 L1 recombinant protein, HPV-11 L1 recombinant protein, HPV-6 truncated L1 recombinant protein, HPV-11 truncated L1 recombinant protein, for detecting infection by low risk HPV.

The one or more recombinant proteins as described herein can be expressed in various suitable systems, such as bacterial expression systems, viral expression systems, yeast expression systems, mammalian expression systems, e.g., in *E. coli*, yeast, baculovirus, and/or mammalian cell cultures, generally known in the field. Although the polypeptides could be obtained by other means, embodiments of the invention provide one or more recombinant proteins mostly in (or close to) their native forms, which may be a much desirable conformation for binding with antibodies from tissues of human subjects with HPV infection in an immunological assay.

At step 230, the presence of HPV specific antibodies on the clinical sample is detected using a detection antibody. For an antigen array, the detection antibody can be, for example, an anti-human immunoglobulin antibody if a clinical human sample is used. At step 240, the level of the binding between the HPV recombinant proteins and the HPV specific antibody present in the clinical sample is measured for the presence of HPV infection in the clinical sample.

The one or more protein chip assays, immunological assays, nucleic acid assays, as provided herein aims to employ user friendly procedures with simple instrument or no additional instrument to perform in a short period of time. Comparison of the results of the various immunological assays, nucleic acid hybridization assays with cytological and histological data for the human subjects as well as demographic information serve to validate the correlation and accuracy in diagnosing HPV infection and/or cervical cancer.

At present, there are no commercially available protein chip assays or immunological assays to clinically measure the presence of HPV-associated proteins or antibodies. Embodiments of the invention thus provide a diagnostic tool useful for diagnosis of HPV infection and HPV related cervical cancer. In addition, the results from the immunological assays as described herein can be used to compare with other commercially available immunological assays specific designed for p53 and RB. It is known that infection high risk type HPVs, such as HPV-16 and HPV-18 may cause cervical cancer due to the expression of E6 and E7, the viral oncoproteins that induce cervical cell malignancy and alter/reduce the expression of p53 and RB endogenous proteins of the host cells, leading to cellular dysfunction and ultimately carcinoma. Thus, it is contemplated to compare the assay results on the levels of all of these proteins altered by HPV infection performed on clinical samples, e.g., cervical tissues, body fluids, serum, etc., from the same human subjects.

Accordingly, one example of a method of screening a human subject of papillomavirus infection may include obtaining a clinical sample from the human subject, obtaining a first recombinant protein encoded by an early gene of a papillomavirus, obtaining a second recombinant protein encoded by a late gene of the papillomavirus, conducting one or more immunological assays on the clinical sample from the human subject, detecting the presence of an antibody to the first recombinant protein in the human subject using the first recombinant protein, and detecting the presence of an antibody to the second recombinant protein in the human subject using the second recombinant protein. The first recombinant protein may be, for example, recombinant HPV-16 E6 proteins, recombinant HPV-16 E7 proteins, recombinant HPV-18 E6 proteins, recombinant HPV-18 E7 proteins, etc. The second recombinant protein may be, for example, recombinant HPV-16 L1 proteins, and recombinant HPV-18 L1 proteins, among others.

Another example of a method of screening a human subject infected with a human papillomavirus may include obtaining a clinical sample from the human subject, conducting a nucleic acid hybridization assay on the clinical sample, detecting the presence of a papillomavirus genome in the clinical sample from the human subject, conducting one or more immunological assays on the clinical sample, detecting the presence of an antibody to an early papillomavirus viral protein or the presence of the early papillomavirus viral protein in the clinical sample using a first recombinant protein of the early papillomavirus viral protein, and detecting the presence of an antibody to a late papillomavirus viral protein or the presence of the papillomavirus late viral protein in the clinical sample using a second recombinant protein of the late papillomavirus viral protein.

The early papillomavirus viral protein may include, but are not limited to, HPV-16 E6 proteins, HPV-16 E7 proteins, HPV-18 E6 proteins, HPV-18 E7 proteins, HPV-58 E6 proteins, HPV-58 E7 proteins and others. The late papillomavirus viral protein may include, but are not limited to, HPV-16 L1 proteins, HPV-18 L1 proteins, HPV-58 L1 proteins, and others. The presence of the papillomavirus genome can be detected, for example, using a nucleic acid probe with sequence homology to conservative DNA sequences from a papillomavirus gene, including papillomavirus late genes, L1 genes, L2 genes, papillomavirus early genes, E2 genes, E6 genes, and E7 genes, among others.

The one or more diagnostic immunological assays as described therein may include taking a sample of body fluid or tissue likely to contain antibodies against HPV associated proteins and/or HPV antigens, reacting it with one or more recombinant proteins as obtained and described herein, and assaying for the presence of any antibody-antigen complexes by suitable detection systems. Positive results confirm that the clinical sample may contain antibodies to indicate past HPV infection and concentrated levels of the antibodies present in the clinical sample. It is also likely to detect current HPV infection, indicating strong immune response of the human subject.

The one or more diagnostic immunological assays as described therein may also include obtaining polyclonal antibodies, monoclonal antibodies, and/or antiserum specific against the one or more recombinant proteins as obtained and described herein, taking a clinical sample likely to contain HPV associated proteins and/or antigens, reacting it with the obtained polyclonal antibodies, monoclonal antibodies, and/or antiserum specific for the one or more recombinant proteins, and assaying for the presence of any antibody-antigen complexes by suitable detection systems. Suitable detection system may employ various colormetric, chemiluminescent, fluorescent substrates, etc., specific for a secondary antibody used in each immunological assay.

Still, another example of a method of screening a human subject of high risk human papillomavirus infection includes obtaining a clinical sample from the human subject, obtaining a first recombinant protein purified from a first protein expression system with a first expression vector having a portion of nucleic acid sequence corresponding to the full length nucleic acid sequence of an early papillomavirus gene and obtaining a second recombinant protein purified from a second protein expression system with a second expression vector having a portion of nucleic acid sequence corresponding to the full length nucleic acid sequence of a late papillomavirus gene. Then, one or more immunological assays can be conducted on the clinical sample to detect the presence of an antibody to a viral oncoprotein or the presence of the viral oncoprotein in the clinical sample using the first recombinant protein and the second recombinant protein. The first recombinant protein may be, for example, recombinant HPV-16 E6 proteins, recombinant HPV-16 E7 proteins, recombinant HPV-18 E6 proteins, and recombinant HPV-18 E7 proteins, etc. The second recombinant protein may be, for example, recombinant HPV-16 L1 proteins, and recombinant HPV-18 L1 proteins, etc. The early papillomavirus gene may be, for example, papillomavirus E6 genes and papillomavirus E7 genes, etc. The late papillomavirus gene may be, for example, papillomavirus L1 genes and papillomavirus L2 genes, etc. The early and late genes may be derived from high risk human papillomavirus, such as HPV-16 and HPV-18, etc.

Clinically applicable vaccination programs for cervical cancer may be available, as such, early detection to screen HPV positive and negative infected individuals is more than ever an urgent need to search for candidate subjects suitable of being vaccinated. Strategies to prevent cervical cancer may thus requires improved HPV testing/screening to cover a broad range of the worldwide population in addition to closely follow-up those subjects with past or present HPV infection and/or pre-cancerous lesions.

Screening/testing for past or present HPV infection along with a Pap smear can become the standard of care and the need is acknowledged in clinical guidelines developed by major medical groups including the American College of Obstetricians and Gynecologists (ACOG), the American Cancer Society (ACS), the Association of Reproductive Health Professionals (ARHP) and the American Society for Colposcopy and Cervical Pathology (ASCCP). Thus, the invention as described herein can be commercialized as a HPV general infection assay and/or a HPV high risk type infection assay and may play an important role as screening tests for cervical cancer. It is proposed that cervical cancer screening might become more efficient when it is based on combined cytology (results of Pap smear test) and high risk HPV infection screening. HPV infection screening tests may become necessary in addition to cervical cancer screening to serve as an early, quick and easy screening, a quality control for false-negative smears, in triage of women with equivocal smears, in follow-up of women treated for CIN3 or cervical cancer and for the detection of cervical adenocarcinoma.

Early diagnosis of infection with high risk HPV types is important for successful prevention and treatment of cervical cancer, which is one of the more deadly forms of cancer. Importantly, it is known that infection in women for 12-15 years with HPV is required before invasive cancer to develop. It is thus important to be able to assay biomarkers of high risk HPV infection as described herein to pre-screen women early, such that it will be possible to treat HPV infection early and prevent cervical cancer development, rather than having to rely on chemotherapy or radiation to treat cancer malignancy. Developing the immunological assays as described herein to detect a series of biomarkers for general HPV infection in population as well as infection with high risk HPVs can be used for early diagnosis and therefore prevention of cervical cancer.

EXAMPLES

An object of the invention is to develop immune-responsive or antibody-reactive recombinant proteins derived from early genes and/or late genes of various HPV types and strains. It is a further object to provide these recombinant proteins in a chemically pure form. It is a still further object to provide simple, rapid, less expensive and more sensitive assays/tests for diagnosing not only HPV infection, but also most, if not all, HPV-associated neoplasm.

I. Cloning and Production of Recombinant Proteins Encoded by HPV Genes.

Recombinant proteins encoded by early HPV genes and late HPV genes were obtained. Recombinant proteins were obtained by itself or as hybrid proteins fused transcriptionally or translationally to a portion of a full length DNA fragment for a HPV gene of interest. The DNA sequence of the HPV gene of interest was derived from high risk HPV types, low risk HPV types, oncogenic HPV strains within a HPV type, etc. An oncogenic HPV strain is an HPV strain that is known to cause cervical cancer as determined by the National Cancer Institute (NCI, 2001). Oncogenic HPV proteins are early viral proteins encoded by an oncogenic HPV type or strain. The sequences of various HPV viral genes and proteins are also found as database entries at NCBI's Gene Bank database, as follows: HPV16-E6: GI:9627100; HPV18-E6: GI:9626069; HPV31-E6: GI:9627109; HPV35-E6: GI:9627127; HPV30-E6: GI:9627320; HPV39-E6: GI:9627165; HPV45-E6: GI:9627356; HPV51-E6: GI:9627155; HPV52-E6: GI:9627370; HPV56-E6: GI:9627383; HPV59-E6: GI:9627962; HPV58-E6: GI:9626489; HPV33-E6: GI:9627118; HPV66-E6: GI:9628582; HPV68b-E6: GI:184383; HPV69-E6: GI:9634605; HPV26-E6: GI:396956; HPV53-E6: GI:9627377; HPV73: GI:1491692; HPV82: GI:9634614, HPV34 GI:396989; HPV67 GI:3228267; and HPV70 GI:1173493.

Other expression vectors used as recombinant protein overexpression systems with histidine tag (e.g., $His_6$, $His_8$, etc.), glutathione-S-transferase (GST) fusion, maltose-binding-protein (MBP), among others, was also used. In addition, the obtained HPV-16 E6 DNA fragment was sub-cloned into other expression systems, including maltose-binding-protein and glutathione-S-transferase-E6 fusion protein expression systems. Various expression systems was also used to express E6 recombinant proteins from various HPV genotypes types and strains. For example, E6 recombinant protein from HPV-58 was obtained and designated as HPV-58-MBP-E6.

His tagged-HPV16-E6 and MBP-HPV-E6 recombinant proteins were expressed in *E. coli* BL21(DE3) using IPTG driven induction. After two hour induction of protein expression at 37° C., GST-E6 or MBP-E6 recombinant proteins using standard protocols recommended by the suppliers (Amersham and New England Biolabs, respectively) were obtained and purified to a final concentration of about 1 mg/L. Longer induction time and re-flow though on protein purification column were found to generate higher protein yield, resulting in highly concentrated purified recombinant proteins at a yield of about 2-10 mg/L). The purity of the recombinant GST-E6 proteins was estimated to be >90% based on PAGE analysis. Recombinant E6 fusion proteins was used to detect the presence of E6 antibody on clinical samples and was also used as immunogens for production of polyclonal antiserum and monoclonal antibodies.

The molecular weight of the resulting recombinant HPV-16 E7 GST protein is about 37.2 KD. The recombinant HPV-16 E7 GST proteins were obtained and purified to a final concentration of about 1 mg/L. The recombinant HPV-16 E7 HIS proteins were also obtained and purified to a final concentration of about 1 mg/L. Other expression systems were also used to express E7 recombinant proteins from various HPV genotypes types and strains. For example, E7 recombinant protein from HPV-18 was obtained and designated as HPV-18-E7-his. Recombinant E7 fusion proteins or recombinant E7 baculovirus proteins were used to detect the presence of E7 antibody on clinical samples and were also be used as immunogens for production of polyclonal antiserum and monoclonal antibodies.

In general, recombinant proteins from various high risk HPV types and low risk HPV types or strains were obtained by cloning of early and late genes by polymerase chain reaction (PCR) amplification using a pair of forward and reverse primers using procedures as described herein and in various recombinant protein expression systems. For example, a recombinant N-terminal fragment of HPV-16 L1 protein was also obtained by expression in His-tagged expression system. For example, partial and full length L1 recombinant proteins from HPV-16 were obtained from a his-tagged expression system and a baculovirus expression system and designated as HPV-16L1N-his and HPV-16L1-his (baculo-SF9). Recombinant L1 proteins and/or recombinant L1 partial proteins were used to detect the presence of L1 antibody on clinical samples and were also used as immunogens for production of polyclonal antiserum and monoclonal antibodies.

Recombinant fusion proteins were obtained for different HPV types, such as different high risk HPV types, e.g., HPV-16, HPV-18, HPV-58, etc. P1 indicates a purified recombinant HPV-58-E6-MBP fusion protein as compared to P3 for a MBP protein alone. P2 indicates a purified recombinant HPV-16-E7-His fusion protein and CP indicates a purified recombinant HPV-16-E6-His fusion protein.

The E6 and E7 oncoproteins encoded by early E6 and E7 genes were constitutively expressed in tumor cells, and silencing these genes yields reversion of the malignant phenotype. Thus, the early E6 and E7 gene products seem to be the tumor-specific antigens, and the possible targets or probes for screening these proteins/antigens or their antibodies thereof in immunological screening assay. These oncoproteins can also be targets for developing vaccines for immunotherapy to control HPV induced tumors.

For example, antibodies to the E6 and/or E7 oncoproteins have been found in those with HPV associated neoplasms. The E6 and E7 oncoproteins appear to be natural targets for antibody production due to their consistent expression in cervical cancer cells. It has been found that IgG and IgA against HPV-16 E6 and E7 oncoproteins are strongly disease associated. Antibodies against the E6 and E7 oncoproteins are at high levels in sera from cervical cancer patients as compared against non-cancer controls. Moreover, such antibodies can be detectable by immunological means even when present in lesser amounts.

II. Sample Collection

Biological samples to be analyzed using the methods of the invention may be obtained from any mammal, e.g., a human or a non-human animal model of HPV. In many embodiments, the biological sample is a clinical sample obtained from a living subject. In some embodiments, the subject from whom the sample was obtained is apparently healthy, where the analyses and/or assays are performed as a part of routine screening. In other embodiments, the subject is one who is susceptible to HPV, (e.g., as determined by family history; exposure to certain environmental factors; etc.). In other embodiments, the subject has symptoms of HPV (e.g., cervical warts, or the like). In other embodiments, the subject has been provisionally diagnosed as having HPV (e.g. as determined by other tests based on, e.g., pap smears, hybrids capture, PCR tests, etc.).

The biological sample may be derived from any cells, tissues, organs or group of cells of the subject. In some embodiments a cervical scrape, biopsy, or lavage was obtained from a subject. In other embodiments, the sample is a blood or urine sample. In some embodiments, the biological sample was processed, e.g., to remove certain components that may interfere with an assay or method of the invention, using methods that are standard in the art. In some embodiments, the biological sample was processed to enrich for proteins, e.g., by salt precipitation, and the like. In certain embodiments, the sample was processed in the presence of proteasome inhibitor to inhibit degradation of antibodies, proteins, or antigens and the like.

Samples as used herein include to a material or mixture of materials, typically, although not necessarily, in fluid form, i.e., aqueous, containing one or more components of interest and may include any of the biological samples, clinical samples, etc. Samples may be derived from a variety of biological sample, liquid, or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

All samples were taken from female patients during their scheduled visits for gynecological examinations. After inserting a speculum to a human subject, a brush or a cotton swab was inserted in the endocervix and rotated to obtain endocervical cells. The brush or swab was then removed out to smear on a slide Pap smear). The brush or swab was then placed into about 1 ml of specimen dilution buffer (PBS+1% BSA) and vigorously shaken to remove bound material (mucus and cells). The diluted specimens are stored at a −20° or −80° C. freezer.

Venous blood was obtained by usual phlebotomy methods, with a 21- or 22-gauge double-pointed needle into an agar barrier tube for a total of 7-9 ml from each subject. The blood was allowed about 15 minutes at room temperature for clot formation and was centrifuged for 15 minutes. Serum was aspirated away from blood cells, using a disposable pipette, dispensed into Eppendorf tubes as aliquots, and stored at a −20° or −80° C. freezer. As a negative control.

III. Protein Chip Hybridization Assays for Screening of HPV Infection

Antibody tests and antigen tests for detecting antibodies against proteins encoded by early genes (e.g., E6 and E7) and late genes (e.g., L1) were performed. As an example, for detecting the presence of E6, E7, or L1 antibodies in human subjects, the concentrations of recombinant proteins, E6, E7, L1, respectively, needed to detect an anti-E6 antibody were optimized in a microtiter plate immunological assay format. Optimal reaction times, assay sensitivity and variability and conditions needed to semi-quantify the levels of E6, E7, or L1 antibodies were found and assay sensitivity and specificity were calculated. In one embodiment, the sensitivity of the one or more antibody test assays as described herein is in the range of micrograms, such as in the range of nanograms, or even picograms, etc. The specificity of the one or more immunological antibody test assays as described herein is in the range of about 50% or higher, such as about 70% or higher, about 85% or higher, about 90% or higher, about 95% or higher, or about 99% or higher.

As an example, for detecting the presence of E6, E7, or L1 antigens in human subjects, polyclonal and monoclonal antibodies against E6, E7, or L1 using the recombinant E6, E7, or L1 proteins were generated and the formation of immunocomplexes due to the binding between them were validated. Optimal reaction times, assay sensitivity and variability and conditions needed to semi-quantify the levels of E6, E7, or L1 antibodies, respectively, were found and the sensitivity and specificity for the assays were calculated. In one embodiment, the sensitivity of the one or more antigen assays as described herein is between the range of micrograms, such as in the range of nanograms, or even picograms, etc. The specificity of the one or more immunological antigen test assays as described herein is in the range of about 50% or higher, such as about 70% or higher, about 85% or higher, about 90% or higher, about 95% or higher, or about 99% or higher.

As another example, protein chip immunological assays for detecting HPV proteins, such as E6, E7, L1, etc., or antibodies thereof were performed for rapid detection of HPV infection. In addition, protein chip immunological assays were designed to be multiplexed for detecting different protein or antibodies targets as well as in high throughput. The protein chip immunological assays as provided herein were used for diagnosing HPV infection and for rapid detection of certain cervical cancer biomarkers. In general, a surface of a chip is initially covalently bound to antibodies, proteins, or antigens, which have an affinity to bind the target protein of interest in a sample, by using standard surface chemistries.

For example, purified recombinant E6, E7, and L1 proteins are shown herein to be able to attach to surfaces of a chip and selectively detect E6, E7, and L1 antisera in solution. As such, protein chip immunological assays were developed to provide a rapid readout of the presence of antibodies induced by HPV infection in a sample. Similarly, protein chip immunological assays were developed to provide a rapid readout of the presence of viral proteins in a sample due to HPV infection by attaching antisera or antibodies against HPV viral proteins encoded by early genes and/or late genes, e.g., L1, E6 and E7, etc.

To diagnose HPV infection using protein chip immunological assays, a capture agent (e.g., the pre-spotting anti-HPV antibody or the prespoting HPV protein), were attached individually to various positions on the surface of one or more protein chips. Alternatively, the capture agent was attached to different positions and thus in multiplexed format to detect different HPV infection related proteins simultaneously in one sample.

The protein chip array of proteins or antibody from all HPV types, strains, or variants can be generated and used to screen phenotypes of HPV infection. Thus, the use of protein chip assays can be a very powerful screening tool to enable the design of one protein chip or test/assay suitable for executing many or all related immunological assays for screening or diagnosing HPV infection.

The capture agent in a protein chip assay includes, but is not limited to, recombinant HPV viral proteins encoded by HPV early genes and late genes, recombinant E6, E7, and L1 proteins, antisera or antibodies against HPV viral proteins, encoded by early genes and/or late genes, e.g., L1, E6 and E7, etc. The assay conditions for the one or more protein chips were optimized/standardized and tested on clinical samples. The results from the ELISA immunological assays were also checked and correlated with the results of the protein chip immunological assays. The protein chip immunological assays may give better sensitivity over microplate immunological assays because of the use of laser as light source and better instrument designed for better detection limit. The higher assay sensitivity and better detection instrument enable the detection of detect extremely low amounts of antigens or antibody induce or developed in the body of those human subjects who are in the early stage of HPV infection or disease development to provide better prevention and disease management.

Positive results from the assays confirm that the clinical sample may contain HPV associated proteins or antigens to indicate current HPV infection present in the clinical sample. It is also likely to detect past HPV infection still present in the clinical sample by detecting immune response of past or current HPV infection and/or the presence of antibodies induced recently or in the past due to HPV infection, etc. Further, the one or more assays provided herein are suitable for general HPV infection as well as infection by high risk HPV types by using recombinant proteins derived from the genes of the HPV high risk types.

By obtaining the results of the assays performed to detect antibodies or viral proteins derived from HPV early genes and late genes, concurring positive results further confirm HPV infection by conveniently obtaining one sample (more than one sample can also be used). It was found that concurring positive results from the one or more immunological assays performed herein correlate very well to the clinical status of the human subject where the clinical sample is obtained from. For example, concurring positive results were obtained and found in a large collection of clinical samples, to correlate well to the histological stages of cervical intraepithelial neoplasia (CIN), the stages or degrees/grades of the biopsy-confirmed squamous intraepithelial lesions (SIL), the stages of progression toward invasive cancer, carcinoma, and/or adenocarcinoma, the presence of cytological Atypical Glands of Undetermined Significance (AGUS), the presence of Atypical Squamous Cells of Undetermined Significance (ASCUS), etc.

Non-concurring positive results from the two assays for the proteins derived from HPV early genes and late genes may indicate general HPV infection, such as infection of different HPV types as well as cross reactivity with either one of the proteins in the two assays directed to early or late viral proteins. For example, it is found that there are positive results from cross reactivity to viral proteins derived from HPV early genes but negative results and no cross reactivity to viral proteins derived from HPV late genes, and vice versa.

Protein Chip Immunological Assay for Detection of HPV Associated Antigens or Proteins, and or Other Host Cell Proteins in Various Kinds of Samples Protein chip immunological assays were developed to detect HPV proteins present in a clinical sample using antigen tests (Ag tests). FIG. 3A shows the results as tested on samples containing purified recombinant HPV proteins and FIG. 3B show the results as tested on clinical samples, using an exemplary human serum sample which is known as HPV positive. The antibody array was performed on a protein chip pre-spotted with various antibodies: column 1: rabbit polyclonal anti-HPV-16 E6 antibody; column 2, mouse serum as positive control, column 3, rabbit anti-HPV-18 E6 antibody as cross-reactivity control; column 4, normal rabbit serum as negative control. After incubating the protein chip with the sample, a detection antibody mixture containing mouse anti-HPV-16 E6 and anti-HPV-18 E6 antibodies were used. Then, the binding affinity was observed by secondary antibody (anti-mouse Cy3) pre-coupled with detection signal compatible with the use of laser as light source for scanning the presence of HPV-16 E6 in the human serum sample, and the protein chip assay is sensitive to detect only HPV-16 E6 and not HPV-18 E6. (method of antibody chip assay detecting HPV protein)

A mixture of antibodies as the pre-spotted capture agent was used to rapidly detect the presence of HPV early proteins from different HPV genotypes. The antibody array for performing an antigen test was pre-spotted with various antibodies: column 1: each spot pre-spotting with a mixture of mouse monoclonal anti-HPV-16 E6 antibody or mouse monoclonal anti-HPV-18 E6 antibody; column 2, normal mouse serum as negative control, column 3, normal rabbit serum as positive control. The same protein chip was reused in each of the assays performed in FIGS. 4A-4C.

FIGS. 4A-4B shows the results as tested on samples containing purified recombinant HPV-16 E6 proteins, and purified recombinant HPV-18 E6 proteins, respectively, and FIG. 4C shows the results as tested on a clinical human serum sample which is known as HPV positive. After incubating the protein chip with the sample, a detection antibody mixture containing rabbit anti-HPV-16 E6 and anti-HPV-18 E6 antibodies were used. Then, the binding affinity was observed by secondary antibody (anti-rabbit Cy5) pre-coupled with detection signal for laser scanning and detection of the presence of HPV-16 E6 or HPV-18 E6 in the human serum sample, and the protein chip assay was able to detect both HPV-16 E6 (FIG. 4A) and HPV-18 E6 (FIG. 4B). The human clinical sample as shown in FIG. 4C was tested to contain HPV E6 protein, indicating as HPV positive.

Figure 5:
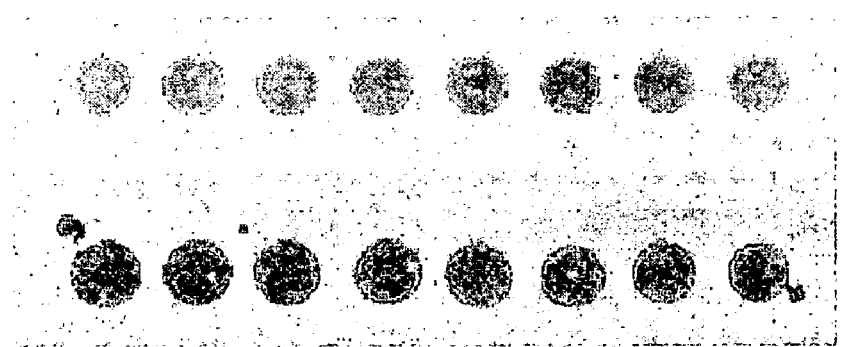
FIG. 5 demonstrates the image results of an exemplary immunological protein chip assay for detecting HPV-16 E7 recombinant protein on a protein chip using various anti-HPV-16 E7 antibodies as spotting antibodies and detecting antibodies.

FIG. 5 shows the results as tested on samples containing purified recombinant HPV-16 E7 proteins on a protein chip pre-spotted with column 1: mouse monoclonal anti-HPV-16 E7 antibody; column 2, normal mouse serum as negative control, column 3, normal rabbit serum as positive control.

FIGS. 6A and 6B shows the results as tested on samples containing purified recombinant HPV-16 E7 protein and purified recombinant HPV-18 E7 proteins, respectively, on a protein chip pre-spotted with column 1: rabbit polyclonal anti-HPV-16 E7 antibody; column 2, normal mouse serum as positive control, column 3, normal rabbit serum as negative control. The specificity of anti-HPV-16 E7 antibody with the sample containing recombinant HPV-16 E7 protein is clearly demonstrated (FIG. 6A) and there is not cross-reactivity with recombinant HPV-18 E7 proteins (FIG. 6B).

Protein Chip Immunological Assay for Detection of HPV Associated Antigens, Proteins, Antibodies and/or Antiserum in Various Kinds of Samples Protein chip immunological assays were also developed to detect antibodies using the purified recombinant HPV proteins, e.g., antibody tests; Ab tests. In addition, the protein chip immunological assay for detecting HPV-associated proteins, HPV-induced antigens, or HPV-specific proteins were performed using purified polyclonal or monoclonal antibodies or antiserum directly or in a sandwiched-type format using a capture antibody and a detection antibody. For example, a pair of antibodies can be used to detect proteins encoded by HPV early and/or late genes from various HPV genotypes in an antigen test (Ag test).

For example, protein chips spotted with purified recombinant proteins, such as HPV-16 E6, HPV-16 E7, HPV-16 L1, HPV-18 E6, HPV-18, E7, HPV-18 L1, HPV-58 E6, etc., as well as positive control proteins and negative control, were tested. As an example, anti-his-tag antibodies were used as positive control for his-tagged recombinant proteins. Examples of negative controls include BSA, his tagged only, MBP only, buffer only, etc. Initially, the conditions were optimized using obtained antibodies, such as monoclonal and polyclonal antibodies against E6, E7, L1 proteins. Varied concentrations of the purified recombinant proteins spotted on the protein chips were used to maximize binding. A secondary antibody coupled to, for example, Cy3 or Cy5, was added to the surface of the protein chips to increase sensitivity. Assay specificity and sensitivity were obtained. Positive controls and negative controls from cell culture samples or clinical samples were also tested.

Synthesized peptides specific for HPV E6, E7, L1 and even p53 and RB proteins were used to coat the surface of the protein chip microarray slide for comparison and obtaining concurrent rapid readout. In addition, commercially available antibody pairs and internal developed antibodies were used to detect p53 and RB in the tested sample. Accordingly, the protein chip immunological assays provide a simple and easy readout of HPV-related proteins (proteins of the HPV early genes and late genes, L1, E6, and E7, as well as HPV regulated p53, RB, p16INK4a and other proteins) in a multiplexed format. These understanding of the results of these assays may provide insight to consequent altered expressions of cellular regulators induced by HPV infection in the host as a signature of infection by high risk HPV types and/or low risks HPV types, which is likely to lead to cervical cancer.

Figure 7:
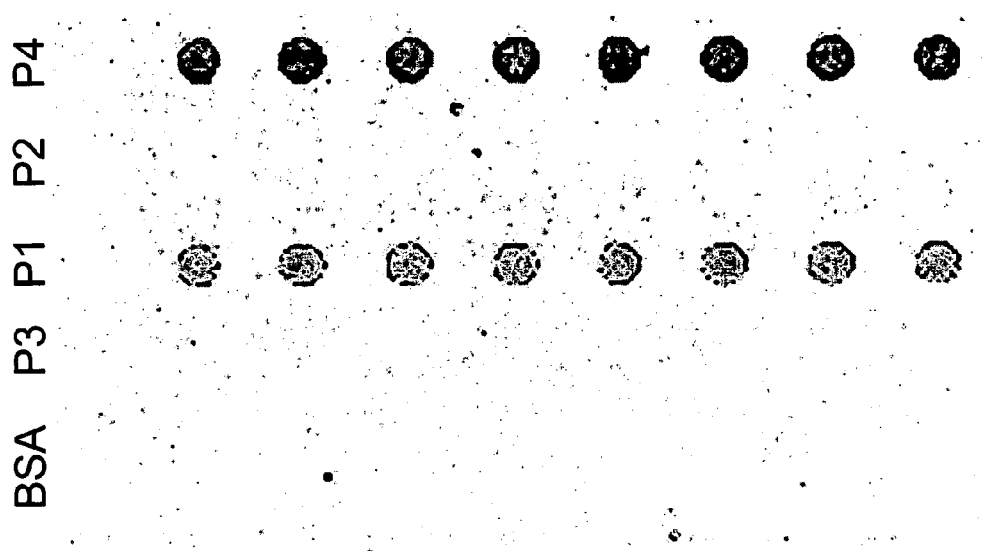
FIG. 7 demonstrates the image results of an exemplary immunological protein chip assay for detecting a monoclonal antibody against E6 oncoprotein using purified recombinant proteins coated on a protein chip. P1 indicates recombinant HPV-58 E6-MBP fusion protein. P3 indicates MBP protein as a control. P2 indicates recombinant HPV-16 E7 his-tag protein. P4 indicates recombinant HPV-16 E6 his-tag protein according to one embodiment of the invention.

FIG. 7 demonstrates the results of an exemplary immunological protein chip assay for detecting a monoclonal antibody against E6 oncoprotein using purified recombinant proteins coated on a protein chip. As shown in FIG. 7, purified recombinant HPV-16-E6 protein (column P4) and HPV-58-E6 protein (column P1) were spotted onto a glass cover slide at a protein concentration of about 100 μg/ml and a solution of test sample was also spotted for a reaction time of about two hours. As a control, purified recombinant HPV-16-E7 protein (column P2), BSA control proteins (column BSA), and recombinant tag-proteins for HPV-58-E6 expression system (column P3) were also attached to the slide. The slide was then reacted with a blocking buffer (PBS/BSA) for 30 min and then reacted with an anti-E6 monoclonal antibody, mAB1-1 (about 5 μgs/ml) for 2 hrs. After the binding reaction, the slide was washed, then dried and reacted with anti-mouse Cy5 (about 4 μgs/ml) for 2 hrs to detect bound a monoclonal anti-HPV-16-E antibody. For example, purified recombinant E6, E7, and L1 proteins are shown herein to be able to attach to surfaces of a chip and selectively detect E6, E7, and L1 antisera in solution. As such, protein chip immunological assays are developed to provide a rapid readout of the presence of antibodies induced by HPV infection in any samples.

As shown in FIG. 7, the monoclonal anti-HPV-16-E6 antibody selectively interacts with the purified recombinant HPV-16-E6 proteins and the purified recombinant HPV-58-E6 (as shown in column P4 and P1, respectively), but not BSA proteins, the purified recombinant HPV-16-E7, nor the recombinant tag-proteins controls (as shown in columns BSA, P3, and P2, respectively). The results indicate that the purified recombinant HPV proteins as provided herein can specifically retain their binding abilities to antibodies in various solid phases and thus it is feasible to further develop the protein chip technology to detect a desirable target agent, such as an antibody, anti-serum in various kinds of samples including clinical samples.

Figure 8:
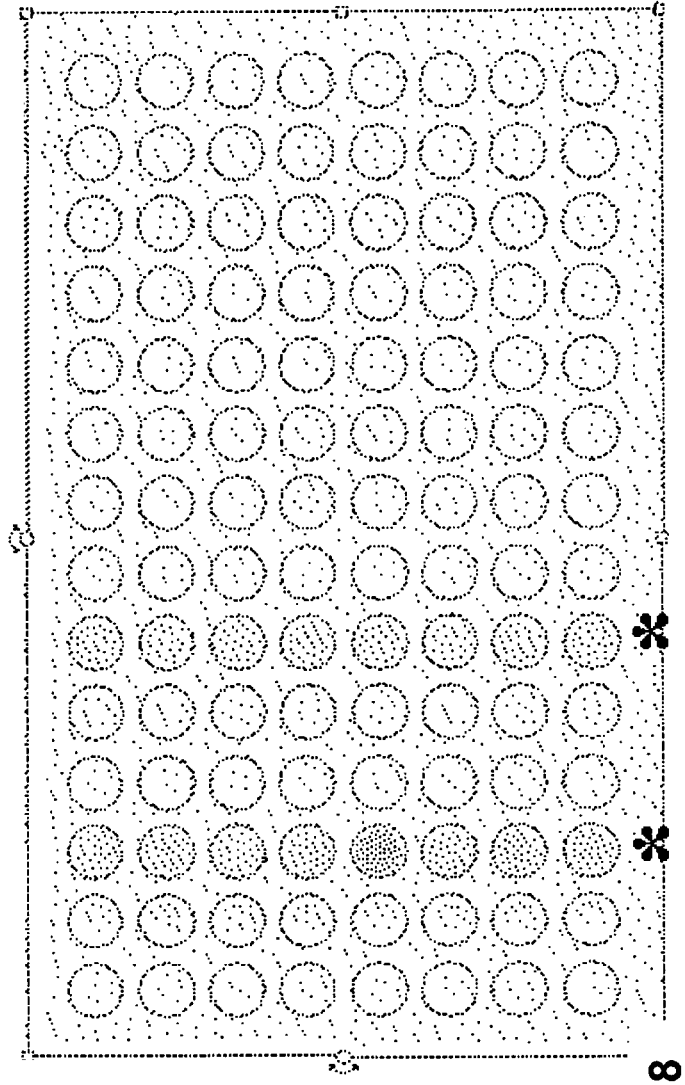
FIG. 8 illustrates the image results of an exemplary protein chip microarray in a format of 14 columns and 8 rows for detecting an anti-HPV E6 monoclonal antibody by performing an antibody test using an immunological protein chip assay.

FIG. 8 illustrates the lay-out of an exemplary slide for performing one or more immunological protein chip assays on the surface of the slide according to one embodiment of the invention. An example, one slide can have a replicate in a matrix format of a microarray (14 columns and 6 rows) and each column or each row can be repetitively coated with the same coating agents, such as purified recombinant proteins, peptides, antibodies, etc. The distance between each coated spot can be varied and is not limiting to any specific length; for example, a distance of about 600 micron between columns and between rows can be used. The slide may also contain one or more bar-codes for identification. A replicate having a matrix format of a microarray of 14 columns and 9 rows can also be used.

FIG. 8 illustrates the image results of an exemplary protein chip microarray in a format of 14 columns and 8 rows for detecting an anti-HPV E6 monoclonal antibody by performing an antibody test using an immunological protein chip assay. Each column was repetitively coated with Column 1, buffer; column 2, 2% BSA control; column 3, P1, HPV 58 E6-MBP recombinant protein; column 4, MBP only recombinant protein control; column 5, HPV 16 E7-his recombinant protein; column 6, HPV 16 E6-his recombinant protein; column 7, 2% histidine buffer control; column 8, HPV 16 E7-GST recombinant protein; column 9, GST recombinant protein control; column 10, HPV 18 E7-his recombinant protein; column 11, 2% histidine buffer control; column 12, HPV 16 L1 N-terminal-his recombinant protein; column 13, HPV 16 L1 full length-his recombinant protein; column 14, baculovirus expression system culture supernatant control. The results in FIG. 8 demonstrate that the purified recombinant HPV 58 E6 protein and the purified recombinant HPV 16 E6 protein coated on the surface of the protein chip microarray can be used to specifically detect an anti-HPV E6 monoclonal antibody.

Figure 9:
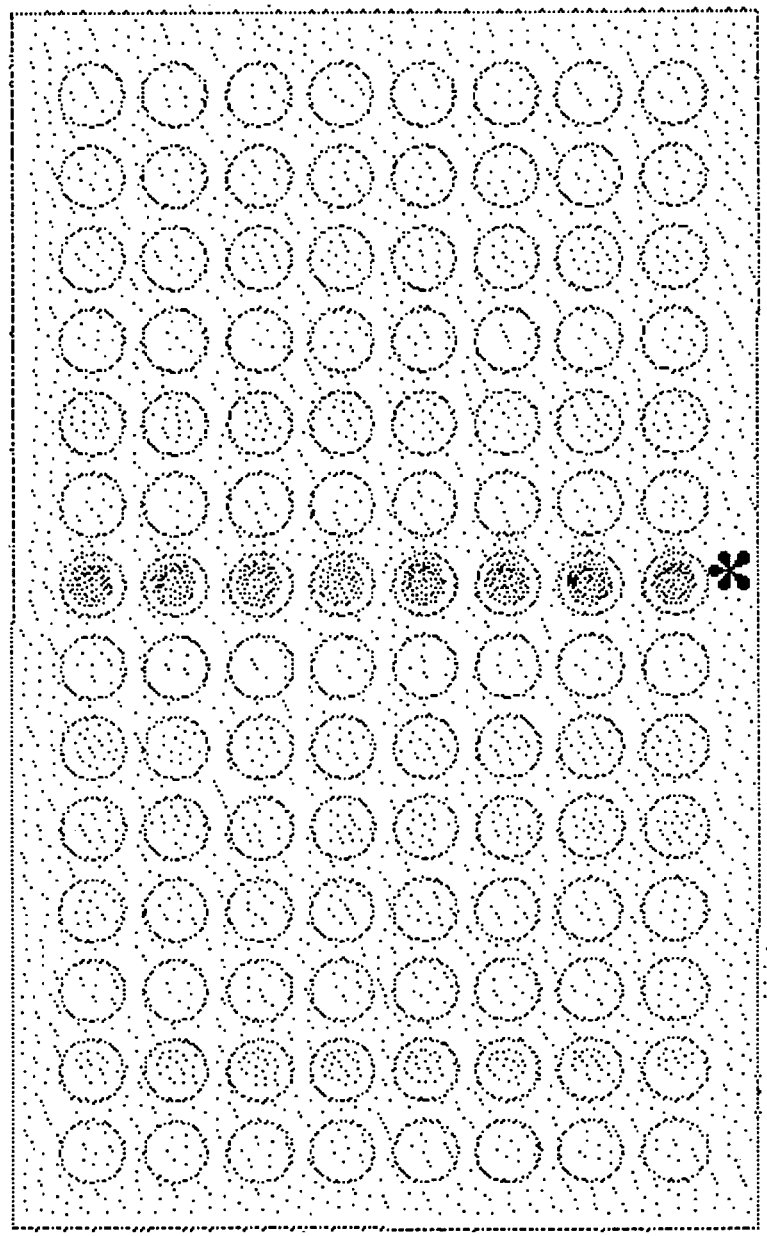
FIG. 9 illustrates the image results of an exemplary protein chip microarray for detecting an anti-HPV E7 monoclonal antibody by performing an antibody test using an immunological protein chip assay.

FIG. 9 illustrates the image results of the exemplary protein chip microarray as shown in FIG. 8 for detecting an anti-HPV E7 monoclonal antibody by performing an antibody test using an immunological protein chip assay. The results in FIG. 9 demonstrate that the purified recombinant HPV 16 E7 protein coated on the surface of the protein chip microarray can be used to specifically detect an anti-HPV 16 E7 monoclonal antibody.

Figure 10:
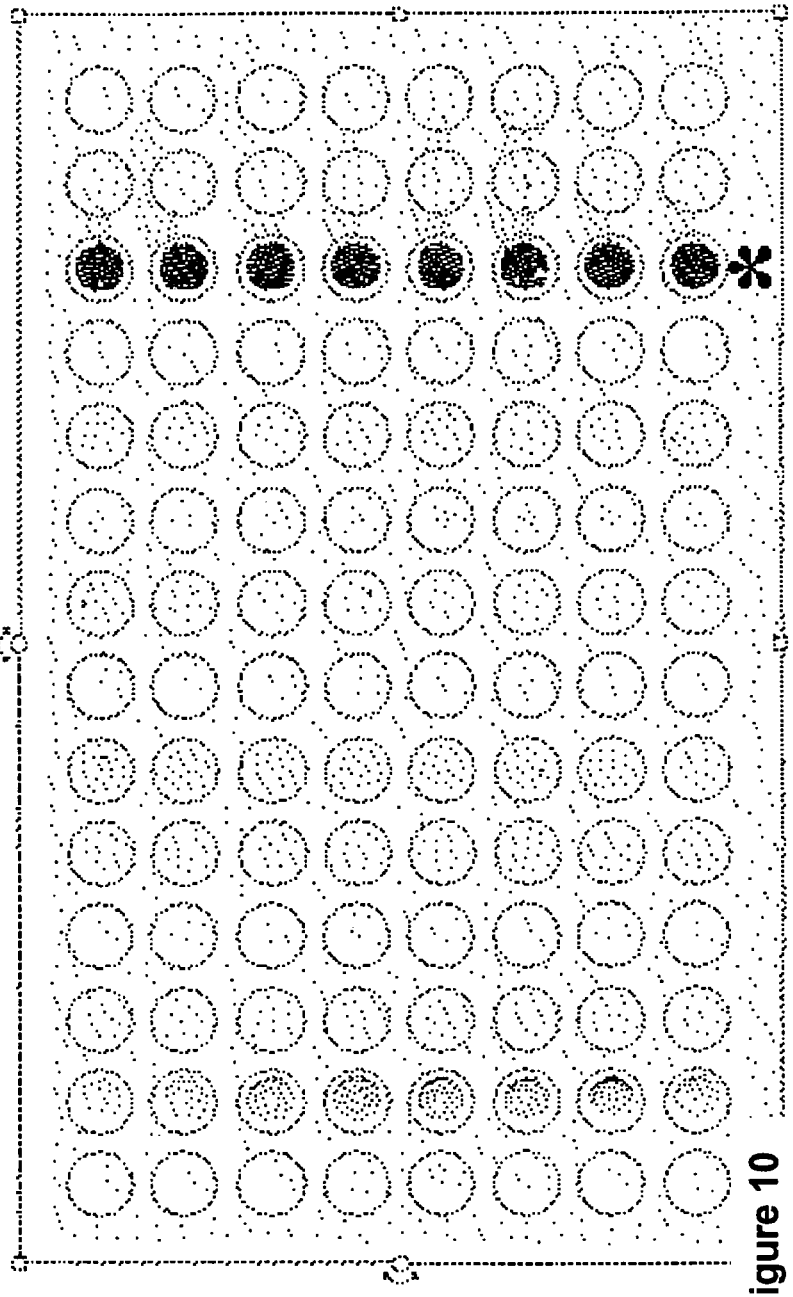
FIG. 10 illustrates the image results of an exemplary protein chip microarray for detecting an anti-HPV L1 monoclonal antibody by performing an antibody test using an immunological protein chip assay.

FIG. 10 illustrates the image results of the exemplary protein chip microarray as shown in FIG. 8 for detecting an anti-HPV L1 monoclonal antibody by performing an antibody test using an immunological protein chip assay. The results in FIG. 10 demonstrate that the purified recombinant HPV 16 L1 protein coated on the surface of the protein chip microarray can be used to specifically detect an anti-HPV L1 monoclonal antibody.

FIG. 11 illustrates the image results of the exemplary protein chip microarray as shown in FIG. 8 for detecting an exemplary anti-his-tagged monoclonal antibody by performing an antibody test using an immunological protein chip assay. The results in FIG. 11 demonstrate that the purified his-tagged recombinant proteins, including HPV 16 E7-his, HPV 16 E6-his, HPV 18 E7-his, and HPV 16 L1 N-terminal-his proteins, coated on the surface of the protein chip microarray can be used to specifically detect an anti-his-tagged monoclonal antibody.

Similarly, protein chip immunological assays were developed to provide a rapid readout of in a clinical sample and to detect the presence of antisera or antibodies against HPV viral proteins encoded by early genes and/or late genes, e.g., L1, E6 and E7, etc. due to HPV infection by attaching the purified recombinant proteins and/or HPV specific peptides.

TABLE 1 laser scanning scores for clinical samples.

| | | Sample #1 | | | Sample #2 Dilution | | | Sample #3 | | |
|---|---|---|---|---|---|---|---|---|---|---|
| | | $10^2$ | 500 | $10^3$ | $10^2$ | 500 | $10^3$ | $10^2$ | 500 | $10^3$ |
| B | Buffer | | | | | | | | | |
| Ctl1 | 2% BSA | | | | | | | | | |
| P1 | HPV 58 E6-MBP | | | | 9 | 4 | 2 | | | 1 |
| Ctl5 | MBP only | | | | 1-2 | 2 | 2 | | | 1 |
| P2 | HPV 16 E7-his | 1 | | 1 | 1-2 | 2 | 1 | 1-2 | 1 | |
| P4 | HPV16 E6-his | | | | 1-2 | 2 | | | | |
| Ctl2 | histidine | | | | | | | | | |
| P5 | HPV 16 E7-GST | | | | 3-4 | 3 | | | | 1 |
| Ctl4 | GST only | | | | | | | | | |
| P7 | HPV 18 E7-his | | | | | | | | | |
| Ctl2 | histidine | | | | | | | | | |
| P8 | HPV 16 L1 N ter-his | | | | 1 | | | | | |
| P9 | HPV 16 L1-his | | | | | | | | | |
| Ctl3 | MBP only | | | | | | | | | |

Figures 12, 13:
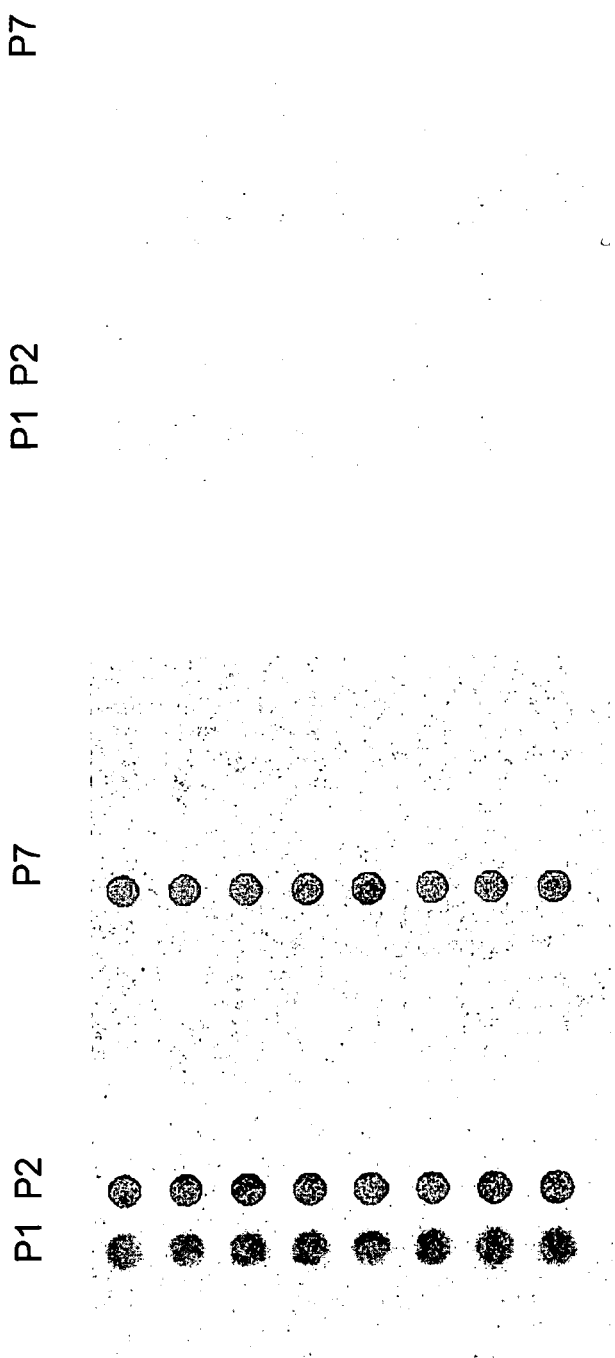
FIG. 12 illustrates the image results of an exemplary protein chip microarray for detecting 1:100 dilution of an exemplary clinical sample.
FIG. 13 illustrates the image results of the exemplary protein chip microarray as shown in FIG. 12 for detecting 1:50 dilution of another exemplary clinical sample.

FIG. 12 illustrates the image results of an exemplary protein chip microarray for detecting 1:100 dilution of a clinical sample, sample #4. As shown in FIG. 12, sample #4 showed positive binding reactivity to the purified HPV 58 E6-MBP (P1), HPV 16 E7-his (P2), and HPV 18 E7-his (P7) recombinant proteins. The results indicate possible infection of high risk HPV types.

FIG. 13 illustrates the image results of an exemplary protein chip microarray for detecting 1:50 dilution of another exemplary clinical sample, sample #3. As shown in FIG. 13, sample #3 showed negative binding reactivity to all the HPV recombinant proteins tested herein. The results indicate possible negative HPV infection.

TABLE 2 laser scanning scores for clinical samples.

| | | Sample #4 | | | Sample #5 Dilution | | | Sample #6 | | |
|---|---|---|---|---|---|---|---|---|---|---|
| | | $10^2$ | 500 | $10^3$ | $10^2$ | 500 | $10^3$ | $10^2$ | 500 | $10^3$ |
| B | Buffer | | | | | | | | | |
| Ctl1 | 2% BSA | | | | | | | | | |
| P1 | HPV 58 E6-MBP | 9 | 3-4 | 2 | 2-3 | | 1 | 0-1 | 0-1 | |
| Ctl5 | MBP only | 1-2 | | | | | | 0-1 | | |
| P2 | HPV 16 E7-his | 6 | 5 | 2 | 1-2 | 1 | 1 | 1-2 | 1 | 1 |
| P4 | HPV16 E6-his | 1 | 1 | | 1 | | | | 1-2 | |
| Ctl2 | histidine | | | | | | | | | |
| P5 | HPV 16 E7-GST | 1 | | | 1 | 1 | | | | |
| Ctl4 | GST only | | | | | | | | | |
| P7 | HPV 18 | 8 | 6 | | | | | | | |

TABLE 2-continued laser scanning scores for clinical samples.

| | | Sample #4 | | | Sample #5 Dilution | | | Sample #6 | | |
|---|---|---|---|---|---|---|---|---|---|---|
| | | $10^2$ | 500 | $10^3$ | $10^2$ | 500 | $10^3$ | $10^2$ | 500 | $10^3$ |
| Ctl2 | E7-his histidine | | | | | | | | | |
| P8 | HPV 16 L1 N ter-his | 1 | | | | | | | | |
| P9 | HPV 16 L1-his | 2 | | | | | | | | |
| Ctl3 | MBP only | | | | | | | | | |

Figure 14:
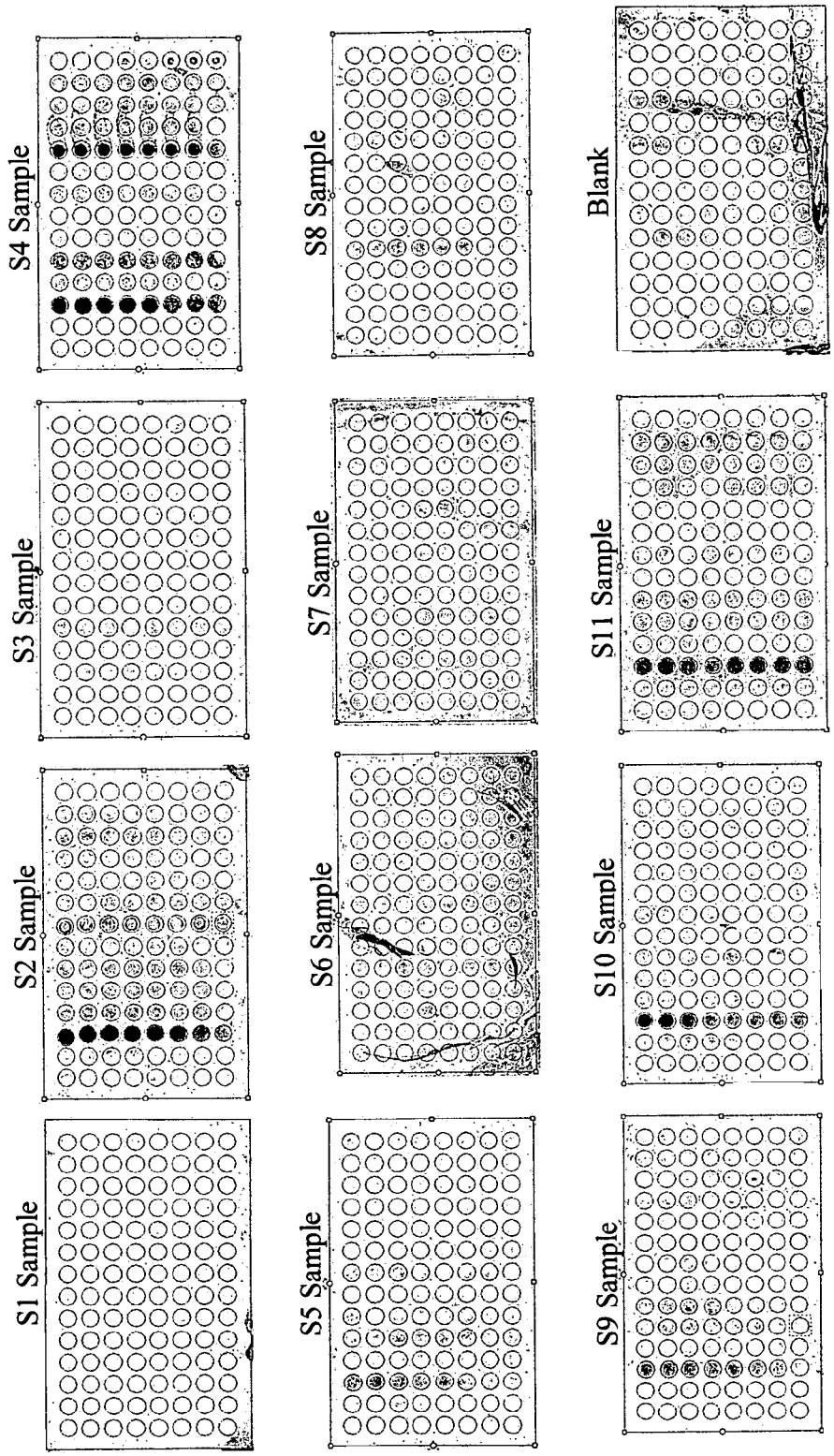
FIG. 14 illustrates the image results of the exemplary protein chip microarray as shown in FIG. 12 for detecting various exemplary clinical samples (samples #1-#11) as compared to a blank sample.
Figure 15:
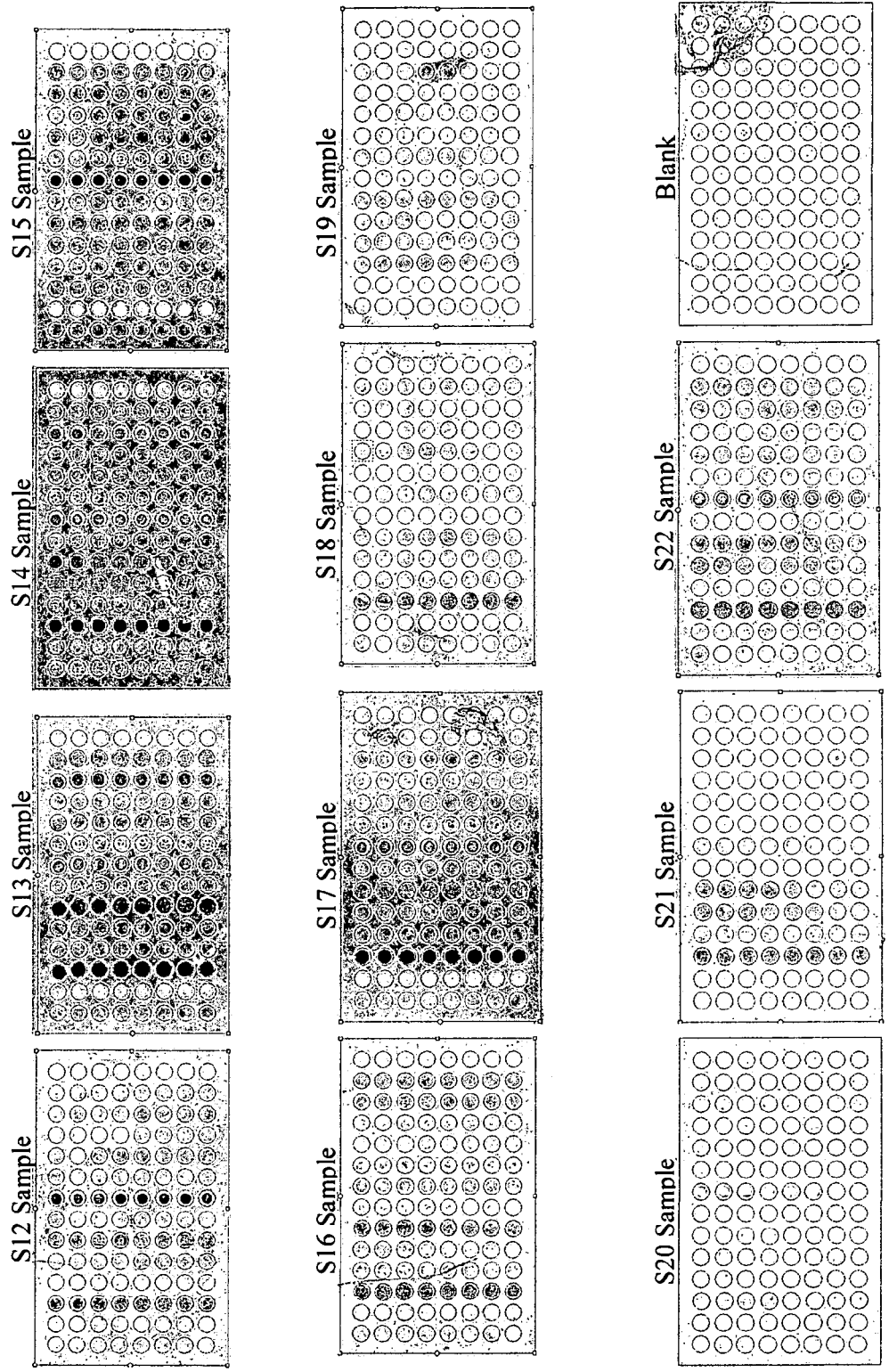
FIG. 15 illustrates the image results of the exemplary protein chip microarray as shown in FIG. 12 for detecting various exemplary clinical samples (samples #12-#22) as compared to a blank sample.

FIG. 14 illustrates the image results of the exemplary protein chip microarray for detecting various exemplary clinical samples (samples #1-#11) as compared to a blank sample. FIG. 15 illustrates the image results of the exemplary protein chip microarray for detecting various exemplary clinical samples (samples #12-#22) as compared to a blank sample. Possible HPV infection can be observed in clinical samples, S2, S4, S5, S9, S10, S11, S12, S13, S14, S15, S16, S17, S18, S21, and S22 with distinctive expression pattern of different HPV proteins and HPV genotypes.

TABLE 3 laser scanning scores for clinical samples.

| | | Sample #7 | | | Sample #8 Dilution | | | Sample #9 | | |
|---|---|---|---|---|---|---|---|---|---|---|
| | | $10^2$ | 500 | $10^3$ | $10^2$ | 500 | $10^3$ | $10^2$ | 500 | $10^3$ |
| B | Buffer | | | | | | | | | |
| Ctl1 | 2% BSA | | | | | | | | | |
| P1 | HPV 58 E6-MBP | | | | 0-1 | 2 | | 3-4 | 2 | |
| Ctl5 | MBP only | | | | 1 | 2 | | | | |
| P2 | HPV 16 E7-his | 1 | 1 | | ~2 | 1 | | 1 | 2 | |
| P4 | HPV16 E6-his | | | | | | | 1-2 | 2 | |
| Ctl2 | histidine | | | | | | | | | |
| P5 | HPV 16 E7-GST | | | | | | | | | |
| Ctl4 | GST only | | | | | | | | | |
| P7 | HPV 18 E7-his | | | | ~2 | | | | | |
| Ctl2 | histidine | | | | | | | | | |
| P8 | HPV 16 L1 N ter-his | | | | | | | | | |
| P9 | HPV 16 L1-his | | | | | | | | | |
| Ctl3 | MBP only | | | | | | | | | |

Tables 1-7 demonstrate the sensitivity of the protein chip assays and illustrate the laser scanner scored results of an exemplary protein chip microarray prespotted with various recombinant proteins for detecting different concentrations of an anti-HPV antibody in the clinical samples according to one embodiment of the invention. Various concentrations (dilution 1:100, 1:500, & 1:1000) of various exemplary clinical samples (samples #1-#3) were tested according to one embodiment of the invention.

It is known that infection high risk type HPVs, such as HPV-16 and HPV-18 may cause cervical cancer due to the expression of E6 and E7, the viral oncoproteins that induce cervical cell malignancy and alter/reduce the expression of p53 and RB endogenous proteins of the host cells, leading to cellular dysfunction and ultimately carcinoma. Thus, it is contemplated to compare the assays results on the levels of all of these proteins altered by HPV infection perform on clinical samples, e.g., cervical tissues, body fluids, serum, etc., from the same human subjects.

TABLE 4 laser scanning scores for clinical samples.

| | | Sample #10 | | | Sample #11 Dilution | | | Sample #12 | | |
|---|---|---|---|---|---|---|---|---|---|---|
| | | $10^2$ | 500 | $10^3$ | $10^2$ | 500 | $10^3$ | $10^2$ | 500 | $10^3$ |
| B | Buffer | | | | | | | | | |
| Ctl1 | 2% BSA | | | | | | | | | |
| P1 | HPV 58 E6-MBP | 7 | 4 | | 5-6 | 2-3 | | 3-4 | 1-2 | |
| Ctl5 | MBP only | 0-1 | | | | | | | | |
| P2 | HPV 16 E7-his | 1 | 2 | | 1 | 2 | | 1 | 1-2 | |
| P4 | HPV16 E6-his | 1-2 | 1-2 | | 1-2 | 2 | | 2-3 | 1 | |
| Ctl2 | histidine | | | | | | | | | |
| P5 | HPV 16 E7-GST | | | | | 2 | | 6 | 1 | |
| Ctl4 | GST only | | | | | | | | | |
| P7 | HPV 18 E7-his | | | | | | | | | |
| Ctl2 | histidine | | | | | | | | | |
| P8 | HPV 16 L1 N ter-his | | | | | | | | | |
| P9 | HPV 16 L1-his | | | | | 0-1 | | | | |
| Ctl3 | MBP only | | | | | | | | | |

Generally, the antibody used has a detection limit of about 50 ng/ml or lower, such as about 50 pg/ml or lower. The clinical sample can normally be diluted to 1:1000 and thus, demonstrating the assays herein are very sensitive. For example, sample # 2, # 3, # 4, # 5, # 6 and # 15 were diluted to 1:1000. But the best results were obtained at about 1 to 100 dilution.

Changes in the expression levels among these proteins affected by HPV infection (e.g., E6, E7, p53, Rb, among others) serve as a signature for high risk of contracting cervical cancer. Elevated levels of HPV-associated viral proteins or antigens and reduced levels of p53 and RB confirm the human subjects of not just HPV infection but also at high risk of contracting cervical cancer. On the contrary, unchanged levels of p53 and RB in the human subjects but elevated levels of HPV-associated viral proteins or antigens may indicate a general HPV infection and cervical cancer is not yet progressed.

TABLE 5 laser scanning scores for clinical samples.

| | | Sample #13 | | | Sample #14 Dilution | | | Sample #15 | | |
|---|---|---|---|---|---|---|---|---|---|---|
| | | $10^2$ | 500 | $10^3$ | $10^2$ | 500 | $10^3$ | $10^2$ | 500 | $10^3$ |
| B | Buffer | | | | | | | | | |
| Ctl1 | 2% BSA | | | | | | | | | |
| P1 | HPV 58 E6-MBP | 10 | 5 | | 10 | 5 | | 4 | 2 | 1 |
| Ctl5 | MBP only | 2 | 3 | | | | | | | |
| P2 | HPV 16 E7-his | 3 | 4 | | 3 | 3 | | 3 | 2 | 1 |
| P4 | HPV16 E6-his | 7 | 4 | | 5 | 3 | | 4 | 1 | |

TABLE 5-continued laser scanning scores for clinical samples.

| | | Sample #13 | | | Sample #14 | | | Sample #15 | | |
|---|---|---|---|---|---|---|---|---|---|---|
| | | | | | Dilution | | | | | |
| | | $10^2$ | 500 | $10^3$ | $10^2$ | 500 | $10^3$ | $10^2$ | 500 | $10^3$ |
| Ctl2 | histidine | | | | | | | | | |
| P5 | HPV 16 E7-GST | 4-5 | 4 | | 4 | 4 | | 10 | 6 | 3 |
| Ctl4 | GST only | | | | | | | | | |
| P7 | HPV 18 E7-his | 3 | | | 3 | | | 1-2 | | |
| Ctl2 | histidine | | | | | | | | | |
| P8 | HPV 16 L1 N ter-his | 5 | 2 | | 4 | 2 | | 3 | 0-1 | |
| P9 | HPV 16 L1-his | 3 | 1 | | 4 | 1 | | 4 | 1 | |
| Ctl3 | MBP only | | | | | | | | | |

Figure 16:
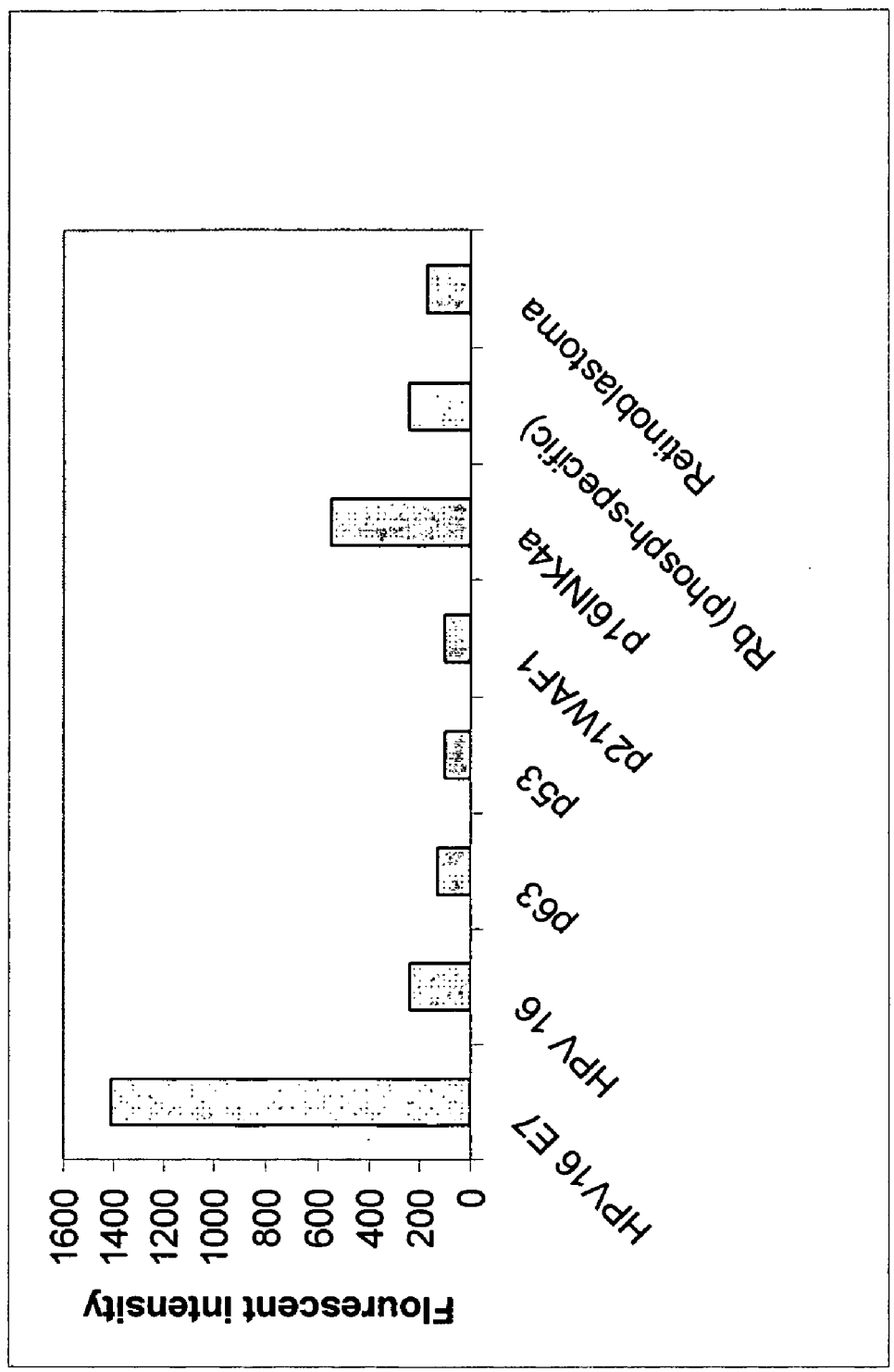
FIG. 16 illustrates the laser scanner scored results of the exemplary protein chip microarray as shown in FIG. 12 for detecting various concentrations (dilution 1:100, 1:500, &

FIG. 16 shows the results of protein chip assays for detecting the presence of various HPV proteins and host cell proteins. An antibody array pre-spotted with antibodies against HPV and various cell proteins were used to detect the presence of these HPV proteins and host cell proteins in a human cervical scrape clinical sample known to be keratinizing squamous cell carcinoma (grade 3). Binding of the proteins from the human sample with prespotted antibody against proteins such as HPV-16 E7, HPV-16 L1, p63, p53, p21WAF1, p16INK4a, phosphorylated Rb, and unphosphorylated Rb were analyzed. Changes in the expression levels of among these proteins affected by HPV infection were observed with an increased level of HPV-16 E7, HPV-16 L1, and p16INK4a.

TABLE 6 laser scanning scores for clinical samples.

| | | Sample #16 | | | Sample #17 | | | Sample #18 | | |
|---|---|---|---|---|---|---|---|---|---|---|
| | | | | | Dilution | | | | | |
| | | $10^2$ | 500 | $10^3$ | $10^2$ | 500 | $10^3$ | $10^2$ | 500 | $10^3$ |
| B | Buffer | | | | | | | | | |
| Ctl1 | 2% BSA | | | | | | | | | |
| P1 | HPV 58 E6-MBP | 5 | 2 | | 10 | 4-5 | | 3-4 | 0-1 | |
| Ctl5 | MBP only | 1-2 | | | | | | | | |
| P2 | HPV 16 E7-his | 3 | 2 | | 2 | 2 | | 1 | 1-2 | |
| P4 | HPV16 E6-his | 4 | 1 | | 5 | 2 | | 1-2 | | |
| Ctl2 | histidine | | | | | | | | | |
| P5 | HPV 16 E7-GST | 2 | | | 5 | 1-2 | | 1 | 1-2 | |
| Ctl4 | GST only | | | | | | | | | |
| P7 | HPV 18 E7-his | | | | | | | 1 | | |
| Ctl2 | histidine | | | | | | | | | |
| P8 | HPV 16 L1 N ter-his | 3 | | | 1-2 | | | | | |
| P9 | HPV 16 L1-his | 4 | | | | | | 0-1 | | |
| Ctl3 | MBP only | | | | | | | | | |

IV. Immunological Assays for Screening of HPV Infection

One of the initial reactions of a human subject to HPV infection is thought to be the generation of antibodies against the E6 and E7 oncoproteins. Presently, no immunological diagnostic assay is commercially available to detect this immune response. Because the amino acid sequences of various E6 and E7 proteins (see, Table 8) are different with various degree of amino acid sequence homology among different HPV types, host antibodies produced in response to the same early oncoprotein from one HPV type will be very different from another HPV type. For example, antibodies induced in a host against oncoproteins (e.g., E6, E7, etc.) from an oncogenic HPV type or strain (e.g., HPV-16, HPV18, etc.) can be significant different from antibodies induced by other proteins associated with other HPV types.

TABLE 7 laser scanning scores for clinical samples.

| | | Sample #19 | | | Sample #20 | | | Sample #21 | | |
|---|---|---|---|---|---|---|---|---|---|---|
| | | | | | Dilution | | | | | |
| | | $10^2$ | 500 | $10^3$ | $10^2$ | 500 | $10^3$ | $10^2$ | 500 | $10^3$ |
| B | Buffer | | | | | | | | | |
| Ctl1 | 2% BSA | | | | | | | | | |
| P1 | HPV 58 E6-MBP | 2-3 | 1 | | 4 | 2 | | 4 | 1 | |
| Ctl5 | MBP only | 2 | 1-2 | | | | | | | |
| P2 | HPV 16 E7-his | 2 | 2 | | 2 | 2 | | 3 | 2 | |
| P4 | HPV16 E6-his | 2 | 2 | | 2 | 1 | | 3 | 1 | |
| Ctl2 | histidine | | | | | | | | | |
| P5 | HPV 16 E7-GST | 1 | 2-3 | | 4 | 2 | | | 0-1 | |
| Ctl4 | GST only | | | | | | | | | |
| P7 | HPV 18 E7-his | | 0-1 | | 2 | | | | | |
| Ctl2 | histidine | | | | | | | | | |
| P8 | HPV 16 L1 N ter-his | | 0-1 | | 1 | | | | | |
| P9 | HPV 16 L1-his | | | | 2 | | | | | |
| Ctl3 | MBP only | | | | | | | | | |

It is proposed and tested herein that, detection of antibodies or antigens to oncoproteins encoded by early genes, such as E6 or E7 protein from HPV high risk types in serum, body fluid, or cervical tissues could be an indication whether the human subject is at high risk for cervical cancer development. In addition, detection of antibodies or antigens to viral proteins encoded by late genes, such as capsid proteins L1, L2 from HPV high risk types can be used together or independently in the same or different immunological diagnostic assays to further confirm the risk of the subject to develop cervical cancer.

TABLE 8

Amino acid sequence homology of L1, E6 and E7 for different HPV Types

| | L1 | E6 | E7 |
|---|---|---|---|
| HPV 16 v. HPV 18 | 63% | 53% | 42% |
| HPV 16 v. HPV 31 | 81% | 65% | 73% |
| HPV 16 v. HPV 33 | 79% | 62% | 60% |
| HPV 18 v. HPV 31 | 64% | 51% | 38% |
| HPV 18 v. HPV 33 | 65% | 46% | 44% |
| HPV 31 v. HPV 33 | 78% | 57% | 59% |
| HPV 16 v. HPV 6A | 68% | 35% | 56% |
| HPV 16 v. HPV 11 | 68% | 34% | 55% |
| HPV 6A v. HPV 11 | 92% | 81% | 83% |

Accordingly, embodiments of the invention provide immunological assay systems to detect the presence of any HPV-associated proteins, oncoproteins, and/or capsid proteins directly in one or more immunological assays that can be performed concurrently or separately on an obtained clinical sample. Examples of immunological assay systems and other assays and the results thereof are also described in co-pending U.S. patent application Ser. No. 11/559,366, filed Nov. 13, 2006, which is incorporated by reference herein.

Example

Non-Radioactive Immunological Assays

Cell suspensions from collected samples were centrifuged, and the supernatant was used to run in the assays by diluting the supernatant 1:10 in specimen dilution buffer. Assays from this invention are non-invasive with little or without instruments. In general, embodiments of the invention provides in vitro enzyme immunological assays which are non-radioactive intended for direct detection of HPV associated proteins and/or antibodies as an indication of HPV infection. The assays as described herein are suitable as adjunct tests in addition to clinical physical examination, Pap smear tests, biopsies and other clinical tests.

An immunological assay can, for example, be performed in a variety of different ways. Detection of the antibodies that have bound to specific antigens can, for example, be achieved with various antibodies to antibodies (anti-antibodies) or other compounds with affinity for antibodies, such as protein A or protein G. These reagents can be labeled in many different ways, for example radioactively (radioimmunoassay), with fluorescein (fluoro-immunoassay), or enzymatically (enzyme-linked immunoassay, ELISA or EIA). A special case of enzymatic immunoassay is when the antigen-antibody complexes are detected on clinical samples or tissue sections. Such a procedure is instead referred to as immunostaining or immuno-histocytochemistry, although the underlying principle is the same as for ELISA. In addition, the formats of the immunological assays can vary and may include a format in microplate (various number of wells), simple rapid tests, protein chips, and others.

In an alternate embodiment, the purified recombinant proteins can be used in similar immunological assays to detect the presence of antibodies raised against HPV immunotherapy in the serum, or other bodily fluid or tissues, such as those human subjects undergoing anti-HPV vaccine treatment. The detection of the positive results from the samples of a subject undergoing vaccine treatment using the assays as described herein and the purified recombinant proteins is beneficial, for example, can be used to titrate semi-quantitative the serum sample of the subject treated with an anti-HPV vaccine and adjust the dosage of the vaccines.

There are at least three types, but not limited to, of immunological assays depending the target proteins to be detected, including antigen tests, antibody tests, and antigen/antibody immunocomplex tests. For example, a method is provided to detect the presence of antibodies, immunoglobulins, etc., against HPV proteins, such as E6, E7, and/or L1, etc., in a sample from a human subject. The purified recombinant proteins as described herein can be used to detect antibodies against HPV E6, E7, and/or L1 proteins. The method generally includes contacting the purified recombinant proteins with the sample and detecting any binding of the purified recombinant proteins to the sample, wherein binding of the purified recombinant proteins to the sample indicates the presence of HPV-induced or HPV-associated antibodies in the sample and thus possible HPV infection for the subject in the past or current.

The antibodies present in the sample may be antibodies against E6, E7, L1, and other proteins from the same HPV types and strains as the purified recombinant proteins. Alternatively, cross reactivity of the binding of any antibodies in the sample to the purified recombinant proteins may result in the detection of the presence of antibodies from different HPV types or strains and thus indicate HPV infection of different types or strains. However, such cross reactivity needs to be confirmed since sequence homology of some of the HPV proteins from different HPV types are low as shown in Table 1.

Similarly, methods are provided to detect the presence of antigens, HPV-associated proteins, HPV-induced proteins, such as E6, E7, L1, L2, p53, and/or Rb, etc., in a sample from a human subject. The purified recombinant proteins as described herein can be used, for example, in a sandwiched assay to detect these target proteins or antigens. Alternatively, monoclonal antibody, polyclonal antibodies, and antiserum against the purified recombinant proteins can also be obtained and purified to be used in antigen tests, antibody tests, and antigen/antibody immunocomplex tests to indicate possible HPV infection in the past or current by the same or different types or strains for the subject.

Example

Immunological Antibody Test for Detection of HPV Associated Antibodies

In general, immunological assays, such as ELISA assays, rapid test assays, and protein chip assays, etc., were performed according to standard procedures. The 96 well format is a high throughput screening format useful to optimize assay procedures and conditions. Other format with different number of wells or a different metrix of multiple columns and rows can also be used. Positive controls and negative controls were also performed on, for example, serum samples from donor subjects that are positive for HPV infection and virgin subjects without HPV infection. The immunological assays were found to result in high sensitivity, for example, in detecting E6, E7 and L1 antibodies. Initial titration curves were performed and ELISA assays conditions were optimized.

Example

Immunological Antigen Test for Detection of HPV Associated Antigens or Proteins

A pair of antibodies were used as a capture antibody and a detection antibody in an antigen test, such as a sandwiched ELISA assay. Different pairs of antibodies in different combinations of mABs/mABs, polyABs/mABs, mABs/polyABs or polyABs/polyABs were tested as the capture and detection antibodies and the sandwiched ELISA assay conditions were optimized. The capture and detection antibodies were chosen in different monoclonal/polyclonal combination for a secondary antibody to interact and bind to the resulting immunocomplex. If the optimized capture and detection antibodies are both polyclonal antibodies or both monoclonal antibodies, then one of the capture and detection antibodies will be conjugated to be used with immunological assay-derived detection substrates, such as conjugated horse radish peroxidase, and others used in immunological assays. In general, a sandwiched assay in an antigen test is performed according to standard procedures.

The purified recombinant proteins were used to raise antiserum, polyclonal and monoclonal antibodies by injecting to animal species and screening with the recombinant proteins for specific binding. Many convenient animal species were used to prepare the appropriate antisera, and these antisera were used directly. Suitable animal species include mice, rats, rabbits, guinea pigs, or even larger mammals, such as sheep. For administration to such animals, the recombinant proteins are generally administered in the presence of an adjuvant, usually Freund's complete adjuvant, and the polyclonal sera are harvested periodically by standard techniques.

Monoclonal antibodies may be produced using the method of Kohler and Milstein or by more recent modifications thereof by immortalizing spleen or other antibody-producing cells from injected animals to obtain monoclonal antibody-producing clones. HPV positive and negative human serum samples are useful in screening monoclonal antibody producing hybridoma to ensure the specificity of the monoclonal antibody clones. More than one positive clones reactive with purified E6, E7, and L1 are obtained and further injection of the obtained cell cultures to mice or other animal source can be used to produce ascites for purifying the monoclonal antibodies, such as by protein A affinity column chromatography. The purified antibody will be used as either the capture or detection probes or to be conjugated with detection enzymes, such as (HRP, AP, etc.) for substrate detection in an absorbent, fluorescent, or chemiluminescent detection system.

The polyclonal and monoclonal antibodies obtained are useful for diagnosis of HPV infection in cervical biopsies, serum or genital swabs specimen and in assessing disease levels in human or other subjects. In particular, diagnosis using the antibodies of the invention permits identification of patients at high risk for malignant transformation as well as identification of the particular phase of CIN associated with the sample. The antibodies can also be used in analysis of serum to detect HPV virus or to detect the virus in metastases of infected tissue, as well as to monitor the progression of HPV immunotherapy, anti-HPV vaccines, or other therapeutic agents directed to control of HPV infection and/or cervical carcinoma.

The 96-well format is a high throughput screening format useful to optimize assay procedures and conditions. Positive controls and negative controls were also performed on, for example, serum samples from donor subjects that are positive for HPV infection and virgin subjects without HPV infection. Initial titration curves were performed and protein chip assays conditions were optimized. The immunological assays were found to result in high sensitivity, for example, in detecting various HPV genotypes and E6, E7 and L1 proteins.

Anti-E6, anti-E7, and anti-L1 capture antibody were attached to the bottoms of the microtiter plate for coating before the purified recombinant proteins were added. Then a detection antibody was used to detect the captured recombinant protein bound to the capture antibody. Optimized capture and detection antibody concentrations were identified. The concentration of the recombinant proteins in the reaction resulting in linearity in the assay for antigen detection was determined. These sandwiched assays were repeated multiple times on the same day, as well as on different days to determine assay reproducibility and reliability. Specificity and sensitivity for each assay were determined. Furthermore, the sandwiched assay was shown to have selectivity in detecting cervical cancers versus other cancers, for example, to demonstrate non-cross reactivity with samples from ovarian or endometrial cancers. Since it is known that HPV is found in most if not all cervical cancer cells, but is usually not associated with other cancers, the antigen tests as described herein should not detect antigens associated with other cancers. To test for this selectivity, for example, extracts from tissues of ovarian and endometrial cancer cell lines can be tested and can also serve as negative controls in the antigen tests.

Because most of the samples assayed herein are from genital swabs of a subject, it is possible that the subject may have sexually transmitted disorders and therefore infected with organisms such as Chlamydia/Gonorrhea (bacteria) and Candida (fungi), non-cross reactivity with antigens from other sexually transmitted organisms or other viruses besides HPV are tested. Human serum samples from HPV infected patients and HPV negative subjects were also tested in the antigen tests. As an example, antigen tests were performed to detect the presence of HPV E6, E7, and L1 proteins in a clinical sample.

Example

One-Step Rapid Immunological Assay for Detection of HPV Associated Antigens, Proteins, or Antibodies The one-step rapid immunological assay as provided herein is a non-invasive and easy to run assay, similar to the types of over-the-counter pregnancy tests and without the need of any particular test instrument. The one-step rapid immunological assay can be an in vitro immunochromatographic assay for direct, qualitative detection of common HPV antigens, specific antigens for high risk HPV types, or HPV associated antibodies. The one-step rapid Immunological assay can be used as an adjunct test to Pap smear examination, as point-of-care diagnosis, and/or small clinics or labs. The one-step rapid Immunological assay is suitable for testing condition at room temperature to simply add an obtained sample with or without dilution, wait for a reaction time period for the designed reactions to occur, and score the results, for example, visualization of the results.

The one-step rapid immunological assay may be a membrane or stick test striped with a capture agent, e.g., purified HPV antibodies, recombinant proteins, or HPV-associated antibodies and proteins, etc., as described herein to capture a target agent, e.g., HPV-associated antibodies and HPV-associated proteins, etc., in the clinical sample, followed by an immunoassay detection system.

The one-step rapid immunological assay was performed vertically on a membrane or lateral in a strip. The lateral flow-through or diffusion one-step rapid immunological assays may also referred as immunochromatographic strip tests that take about 5-15 minutes to obtain results and are easy to use, requiring limited training and does not require instrumentation. The basic principles of the assay include a solid phase nitrocellulose membrane or strip containing the capture agent to react with a swab sample from a Pap smear. If the patient sample contains the target agent, then the capture agent in the nitrocellulose membrane reacts with the target agent, and a complex is formed and migrates in the nitrocellulose membrane through diffusion or capillary action.

At a set location in the nitrocellulose membrane or strip, colored particles coupled with anti-human (or anti-mouse or anti-rabbit for antigen detection) immunoglobin are disposed. If the samples contain anti-HPV antibody, the color particle coupled with anti-human (or anti-mouse or anti-rabbit for antigen detection) immunoglobin antibody may react with anti-HPV antibody and form a sandwich-type immunocomplex on the solid phase nitrocellulose membrane or strip, resulting in a visible band. If no target agent is present in the samples, there will be no visible band. All tests may or may not include an internal procedural positive and negative control lines used to validate the test results. Appearance of reactive colored lines, therefore, indicates a positive result, while a negative test produces only one or no line. Therefore, the presence of the target agent in samples can be quickly detected. The assay can be very sensitive and the nitrocellulose membranes, strips, or other suitable membranes or strips are generally very stable, for example, may last months if kept dry and away from heat.

The membrane or stick can also be administered to test human subject during sample collection and/or combined with the cotton swabs, independently or together, to allow the designed immunological reactions to start and thus obtain the test results instantly, for example, right after insertion of a speculum and the swab into the endocervix of the test human subject. Thus, the one-step rapid immunological assay can serve as a primary screening test. The one-step rapid immunological assay can be performed before additional HPV confirmatory tests, including conventional Pap smear cytological tests, the immunological assays and nucleic acid hybridization assays as described herein, or combinations thereof.

Similar procedures and reactions condition as used in the antigen tests and antibody tests as described herein were employed for the one-step rapid immunological assay. Purified recombinant proteins as provided herein were used to impregnate a nitrocellulose membrane or strip. To the other end of the strip, colored particles coupled with anti-human immunoglobin antibody were disposed. Samples were added and reaction conditions were optimized. Negative controls include one or more positions on the membrane or strip without the purified recombinant proteins or with only BSA, serum proteins, or other negative control proteins. Assay specificity and sensitivity were determined and detection of ng/ml range of the target agent is a good range for commercialization.

V. Comparison of the Results of Protein Chip Immunological Analyses with the Results from Other Immunological Analyses ELISA (or EIA) assays were also performed according to standard procedures and were performed, for example, in 96-well microtiter plate. For example, coating of purified recombinant proteins was performed in about 50 µl volume in a 96 well format at 4° C. overnight before blocking the bottoms of a microtiter ELISA plate with about 200 µl of a blocking buffer at room temperature for 2 hours. A sample that contains antiserum, monoclonal antibodies, polyclonal antibodies, and other targeted HPV-induced antibodies was added to react with the recombinant proteins in about 50 µl volume at room temperature before washing with a wash buffer several times. A secondary antibody, anti-human or anti-mouse, etc., that can generically bind to the targeted antibody was used to react with antibodies or immunocomplex bound to the bottom of the microtiter plates. Substrate development was performed and read out in a microtiter plate reader to measure OD absorbance at 450 nm wavelength, $OD_{450}$. In a horseradish peroxidase immunoassay detection system, about 50 µl of 3,3',5,5'tetramethylbenzidine, a substrate for horseradish peroxidase was added to each well of the microtiter plates and the reaction mixture was incubated at room temperature for about 5-30 minutes or until a visually obvious green-blue color developed before stopping the reaction mixture by adding about 50 µl of 1.5 M $H_2SO_4$ into each well.

An ELISA assay (see, e.g., Harlow and Lane (Antibodies: A Laboratory Manual Cold Spring Harbor Laboratory, Cold Spring Harbor, N.Y. (1989)) generally includes preparing proteins/antigens/antibodies, coating the well of a 96 well multiwell plate (microtiter plate) with the antigens/proteins/antibodies, adding proteins of interest or antibodies of interest or conjugated to a detectable compound such as an enzymatic substrate (e.g., horseradish peroxidase or alkaline phosphatase) to the wells and incubating for a period of time, and detecting the presence of the antigens/proteins/antibodies. In some cases, the antibody of interest does not have to be conjugated to a detectable compound; instead, a second antibody (which recognizes the antibody of interest) conjugated to a detectable compound may be added to the well. Also, instead of coating the well with the antigen, the antibody may be coated to the well. In this case, a second antibody conjugated to a detectable compound may be added following the addition of the antigen of interest to the coated well. One of skills in the art would be knowledgeable as to the parameters that can be modified to increase the signal detected as well as other variations of ELISAs known in the art.

An ELISA procedure can also be carried out in a variety of formats. Methods for enhancement of ELISA sensitivity using several layers of anti-antibodies, avidin-biotin complexes and enzyme-anti-enzyme antibody complexes are well known in the art. The solid support or surface for fixation of antigen is usually plastic, as described here, but a variety of other solid supports such as latex or agarose have been described. It is also not necessary for the antigen to be directly fixed onto the solid support/phase. There is for example a commonly used ELISA format that fixes the specific antigen to the solid support via a solid-phase-fixed antibody to the antigen, so-called catching antibody ELISA or sandwich ELISA. A special case of immunoassay which involves a blotting (transfer) of antigen to a solid support in sheet format is termed immunoblotting. Typically, the solid support is nitrocellulose or nylon membranes/sheets, but other supports have been described. Various binding, mixing, incubating, coating, or blotting interactions are involved in an ELISA assay. Prior to an ELISA assay, the antigens or antibodies can be separated according to their sizes by gel electrophoresis or similar methods. Detection of antibodies bound to the specific antigen on the sheet can be carried out in similar ways as for other immunoassays.

FIG. 17 illustrates the comparison and correlation between the results of the ELISA antibody test assays and the results of the protein chip microarrays for various clinical samples (samples #1-#22) according to one or more embodiments of the invention. Overall, the positive results observed from the protein assays were also shown as ELISA positive. The sample #1 was tested negative from both the protein chip assay and the ELISA assay but was tested positive on Digene HG HPV kit. The samples #2-#8 were tested negative on Digene HG HPV kit. Samples #9-#22 were tested positive from both of the protein chip assays and the ELISA assays as well as positive on a PCR L1 assays.

VI. Comparison of the Results of Cytological Analyses with the Results from the Immunological Analyses A large number of clinical samples were obtained for performing immunological assays and/or nucleic acid hybridization assays to screen for HPV infection and the results of the cytological and/or histological assays (such as colposcopy and biopsy) on the obtained clinical samples were also received from hospital collaborators.

ASCUS: Atypical Squamous Cells of Undetermined Significance; unusual or atypical cells in Pap smear, may be inconsequential and significance is underdetermined. AGUS: Atypical Glands of Undetermined Significance. LSIL: Low grade of Squamous Intraepithelial Lesion. HSIL: High grade of Squamous Intraepithelial Lesion. SCC: Squamous Cell Carcinoma. CIN 1: Cervical Intraepithelial Neoplasia, mild cell abnormalities. CIN2: Cervical Intraepithelial Neoplasia with lesions appearing more aggressive. CIN3: Cervical Intraepithelial Neoplasia with aggressive form of dysplasia.

VII. Nucleic Acid Hybridization Assays for Screening of HPV Infection

Nucleic acid hybridization assays were used in addition to the immunological assays provided herein. In general, the hybrid capture II HPV DNA test is an in vitro nucleic acid hybridization assay used for detecting high-risk HPV types by employing RNA probes specific for thirteen high-risk types of HPV. The hybrid capture II HPV DNA test amplifies the presence of RNA:DNA hybridized complex by coating the HPV specific DNA probes to a microtiter plate and a detecting antibody (a monoclonal anti-DNA/RNA hybrid antibody) is used for detecting the amplified RNA:DNA complexes, followed by the addition of chemiluminescent substrates to qualitatively detect the presence of the DNA of the thirteen high-risk HPV types in the sample. Thus, it requires sophisticated equipments and trained personnel to perform the test and analyze the data using specific microplate reader and specific software developed for the reader. The applicability of the hybrid capture technology (Digene tests) is limited because complex execution of techniques requires sophisticated instrumentation and training and false positive and false negative on general population and early HPV infected individuals are very high, probably due to the requirements of the presence of DNA in the test sample which can be easily degraded or lost during sampling or sample-handling. However, the hybrid capture tests can be used to confirm the results of the one or more immunological assays as provided herein. Additional nucleic acid assays, cytological test and/or histological tests are known in the art can be used on the same clinical sample of the invention to further concur the results of the one or more immunological assays

Comparison with HPV DNA Hybrid Capture Assays

Hybrid Capture II HPV DNA Test from Digene Corporation were also performed on obtained clinical samples as a comparison. The hybrid capture II DNA test is approved by the U.S. Food and Drug Administration to test for oncogenic HPV DNA, as reflexive follow-up of an ASCUS (Atypical Squamous Cells of Undetermined Significance) or other abnormal Pap results. The test was run according to the manufacturer's protocol using the microtiter plate based format and probes for "high carcinogenic risk" HPV types at certified clinical laboratories. Samples with readings of 1 fold or more than the positive control (1 pg/mL HPV DNA or 5000 HPV genome copies per test) were considered to contain DNA from a number of high risk HPV types. The hybrid capture test involves a molecular hybridization that uses non-radioactive probes with amplification of the detection of the hybrid ones for chemiluminescence. The material for analysis is denatured and reacts with specific probes forming hybrid RNA/DNA that are captured by antibodies that cover the walls of the tube. Specific antibodies against RNA/DNA conjugated with alkaline phosphatase are reacted with the immobilized RNA/DNA hybrids. By forming a stable substrate complex for alkaline phosphatase, the RNA/DNA hybrids are capture by antibody and detected by chemiluminescence via spectrometry.

Kits can be developed for performing the methods and assays provided herein. Recombinant proteins, antiserum, and antibodies are also provided for developing these assay kits and screening for infection with HPV-16, 18, 31, 33, 35, 45, 52, 58, 59, 66, 68b, 69, 70, 73, 82, etc., types. The kits, the immunological assays, the recombinant proteins, antiserum, and antibodies, etc., as provided herein are useful for a variety of diagnostic analyses, for example, for diagnosing infection by non-oncogenic or oncogenic HPV types or HPV strains in an individual; for determining the likelihood of having cervical cancer, for determining a patient's response to treatment for HPV, for determining the severity of HPV infection in an individual, and for monitoring the progression of HPV in an individual, among others. The kits, the immunological assays, the recombinant proteins, antiserum, and antibodies, etc., as provided herein are useful in the diagnosis of infection with an oncogenic HPV type or a strain of HPV associated with cancers, including cervical, ovarian, breast, anus, penis, prostate, larynx and the buccal cavity, tonsils, nasal passage, skin, bladder, head and neck squamous-cell, occasional peri-ungual carcinomas, as well as benign anogenital warts. The kits, the immunological assays, the recombinant proteins, antiserum, and antibodies, etc., as provided herein are useful in the diagnosis of infection with an oncogenic or a non-oncogenic type or strain of HPV associated with Netherton's syndrome, epidermolysis verruciformis, endometriosis, and other disorders The kits, the immunological assays, the recombinant proteins, antiserum, and antibodies, etc., as provided herein are useful in the diagnosis of infection with an oncogenic or a non-oncogenic HPV type or HPV strain in adult women, adult men, fetuses, infants, children, and immunocompromised individuals.

The kits as described herein can further include, if desired, one or more of various conventional components, such as, for example, containers with one or more buffers, detection reagents or antibodies. Printed instructions, either as inserts or as labels, indicating quantities of the components to be used and guidelines for their use, can also be included in the kit. In the present disclosure it should be understood that the specified materials and conditions are important in practicing the invention but that unspecified materials and conditions are not excluded so long as they do not prevent the benefits of the invention from being realized. Exemplary embodiments of the diagnostic methods of the invention are described above in detail.

In a subject kit, the HPV E6, E7, and/or L1 detection reaction may be performed using an aqueous or solid substrate, where the kit may include reagents for use with several separation and detection platforms such as test strips, sandwich assays, etc. In many embodiments of the test strip kit, the test strip has bound thereto recombinant protein or antibody specific for HPV proteins, and captures HPV induced or HPV associated proteins or antibodies on the solid support. The kit usually includes one or more primary or secondary antibodies for detection, which is either directly or indirectly detectable. The kit may also include components for conducting western blots (e.g., pre-made gels, membranes, transfer systems, etc.); components for carrying out ELISAs (e.g., 96-well plates); components for carrying out immunoprecipitation (e.g. protein A); columns, especially spin columns, for affinity or size separation of proteins or antibodies from a sample. The kit may also contain control samples containing oncogenic or non-oncogenic E6 and/or E7, and/or a dilution series of oncogenic E6 and/or E7, where the dilution series represents a range of appropriate standards with which a user of the kit can compare their results and estimate the level of oncogenic E6 and/or E7 in their sample. Such a dilution series may provide an estimation of the progression of any cancer in a patient. Fluorescence, color, or autoradiogram development results may also be compared to standard curves of fluorescence, color or film density provided by the kit.

Assay conditions suitable for binding are those conditions (in terms of salt concentration, pH, detergent, protein concentration, temperature, etc.) which allow for binding to occur, for example, between a capture agent and a target agent, between a primary antibody and a secondary antibody, between a recombinant protein and a protein or antibody that can bind to the recombinant protein, etc., in solid support or in solution. Such conditions, particularly with respect to antibodies and their antigens, are well known in the art (see, e.g., Harlow and Lane (Antibodies: A Laboratory Manual Cold Spring Harbor Laboratory, Cold Spring Harbor, N.Y. (1989)). Conditions suitable for specific binding typically permit binding partners or pairs that have a dissociation constant ($K_D$) of less than about $10^{-6}$ M to bind to each other selectively.

While the foregoing is directed to embodiments of the present invention, other and further embodiments of the invention may be devised without departing from the basic scope thereof, and the scope thereof is determined by the claims that follow.

The invention claimed is:

1. A method of making an array comprising a recombinant HPV protein selected from the group consisting of a papillomavirus E6 gene product, a papillomavirus E7 gene product, a papillomavirus L1 gene product, and a papillomavirus L2 gene product, comprising the steps of:
    providing a recombinant construct encoding a fusion protein comprising said papillomavirus gene product and an affinity tag selected from the group consisting of a HIS tag, a GST tag, and an MBP tag, wherein said construct does not encode a chaperone;
    expressing said recombinant construct in a host cell;
    incubating an extract prepared from said host cell with an affinity resin under conditions in which said affinity resin specifically binds said affinity tag;
    eluting said recombinant HPV protein from said affinity resin, wherein said expressing of said recombinant construct in said host cell results in a level of protein expression such that said eluting produces a composition comprising said recombinant HPV protein at a concentration of from 1 mg/L to 10 mg/L, wherein
    said recombinant HPV protein is present in said composition at a purity of at least 90% as determined by SDS PAGE, and wherein said recombinant HPV protein is present in said composition in a substantially soluble, monomeric form, as determined by size exclusion chromatography; and
    adsorbing said recombinant HPV protein to a substrate at a defined location on said substrate.

2. The method of claim 1, wherein said expressing, incubating and eluting steps are carried out without the use of a denaturant.

3. The method of claim 1 wherein said papillomavirus is selected from the group consisting of HPV-6, HPV-11, HPV-16, HPV-18, HPV-31, HPV-33, HPV-35, HPV-39, HPV-42, HPV-43, HPV-44, HPV-45, HPV-51, HPV-52, HPV-53, HPV-54, HPV-55, HPV-56, HPV-58, HPV-59, and HPV-66.

4. The method of claim 1, wherein said papillomavirus is selected from the group consisting of HPV-16 and HPV-18.

5. A method for screening a human subject for a papillomavirus infection comprising:
    obtaining a sample from said subject, said sample comprising antibodies produced by said subject;
    contacting said sample with an array wherein said array is made according to the method of claim 1;
    determining the presence, absence, or amount of one or more antibodies in said sample that specifically binds to one or more of a plurality of recombinant HPV proteins; and
    screening said human subject for said papillomavirus infection based on said determined presence, absence, or amount of said one or more antibodies in said sample.

6. The method of claim 5 wherein said papillomavirus infection comprises an infection by one or more viruses selected from the group consisting of HPV-6, HPV-11, HPV-16, HPV-18, HPV-31, HPV-33, HPV-35, HPV-39, HPV-42, HPV-43, HPV-44, HPV-45, HPV-51, HPV-52, HPV-53, HPV-54, HPV-55, HPV-56, HPV-58, HPV-59, and HPV-66.

7. The method of claim 5 wherein said papillomavirus infection comprises an infection by HPV-16 or HPV-18.

* * * * *